United States Patent
Siegel et al.

(10) Patent No.: US 8,354,558 B2
(45) Date of Patent: Jan. 15, 2013

(54) PROCESS FOR DIASTEREOSELECTIVE CONVERSION OF CHIRAL IMINES

(75) Inventors: Wolfgang Siegel, Limburgerhof (DE);
Thilo Hahn, Kirchheimbolanden (DE);
Tobias Staeb, Frankenthal (DE)

(73) Assignee: BASF SE, Ludwigshafen (DE)

( * ) Notice: Subject to any disclaimer, the term of this patent is extended or adjusted under 35 U.S.C. 154(b) by 330 days.

(21) Appl. No.: 12/746,868

(22) PCT Filed: Dec. 10, 2008

(86) PCT No.: PCT/EP2008/067191
§ 371 (c)(1),
(2), (4) Date: Jun. 8, 2010

(87) PCT Pub. No.: WO2009/080511
PCT Pub. Date: Jul. 2, 2009

(65) Prior Publication Data
US 2010/0274053 A1    Oct. 28, 2010

(30) Foreign Application Priority Data
Dec. 21, 2007  (EP) .................................. 07150290

(51) Int. Cl.
*C07C 209/52*    (2006.01)
(52) U.S. Cl. ........................ 564/489; 564/415
(58) Field of Classification Search .................. 564/415, 564/489
See application file for complete search history.

(56) References Cited

U.S. PATENT DOCUMENTS

| | | | |
|---|---|---|---|
| 5,073,648 | A | 12/1991 | Hagishita et al. |
| 6,720,454 | B1 | 4/2004 | Steiner et al. |
| 2008/0167500 | A1 | 7/2008 | Broxterman et al. |

FOREIGN PATENT DOCUMENTS

| | | |
|---|---|---|
| DE | 37 17 111 | 11/1987 |
| DE | 44 28 004 | 2/1996 |
| DE | 198 26 396 | 12/1999 |
| EP | 0 383 132 | 8/1990 |
| EP | 0 443 606 | 8/1991 |
| WO | 01 09080 | 2/2001 |
| WO | 2006 008171 | 1/2006 |
| WO | 2006 030017 | 3/2006 |

OTHER PUBLICATIONS

U.S. Appl. No. 12/808,268, filed Jun. 15, 2010, Staeb, et al.

*Primary Examiner* — Brian J Davis
(74) *Attorney, Agent, or Firm* — Oblon, Spivak, McClelland, Maier & Neustadt, L.L.P.

(57) ABSTRACT

Diastereoselective conversion of chiral imines of the formula I to amines of the formula II

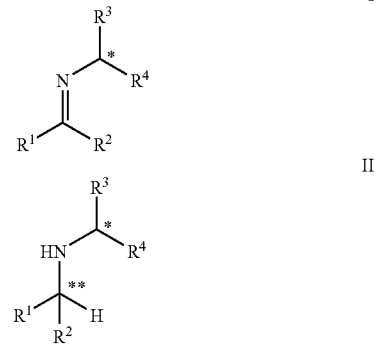

where the $R^1$ to $R^4$ radicals are each as defined in the description and $R^1$ and $R^2$ are different than one another, by converting the imine of the formula I in the presence of hydrogen and a heterogeneous copper-containing catalyst.

16 Claims, No Drawings

PROCESS FOR DIASTEREOSELECTIVE CONVERSION OF CHIRAL IMINES

The present invention relates to a process for diastereoselective conversion of chiral imines of the formula I to amines of the formula II

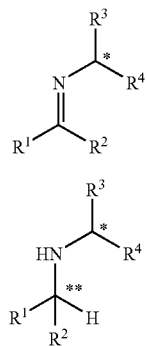

where
$R^1$, $R^2$ are each $C_1$-$C_6$-alkyl, $C_3$-$C_6$-cycloalkyl, $C_2$-$C_6$-alkenyl, $C_2$-$C_6$-alkynyl, $C_2$-$C_6$-haloalkenyl, $C_2$-$C_6$-haloalkynyl, $C_1$-$C_6$-alkoxycarbonyl, $C_3$-$C_6$-alkenyloxycarbonyl, $C_3$-$C_6$-alkynyloxycarbonyl, aminocarbonyl, $C_1$-$C_6$-alkylaminocarbonyl, $C_3$-$C_6$-alkenylaminocarbonyl, $C_3$-$C_6$-alkynylaminocarbonyl, $C_1$-$C_6$-alkylsulfonyl-aminocarbonyl, di($C_1$-$C_6$-alkyl)aminocarbonyl, N—($C_3$-$C_6$-alkenyl)-N—($C_1$-$C_6$-alkyl)aminocarbonyl, N—($C_3$-$C_6$-alkynyl)-N—($C_1$-$C_6$-alkyl)aminocarbonyl, N—($C_1$-$C_6$-alkoxy)-N—($C_1$-$C_6$-alkyl)aminocarbonyl, N—($C_3$-$C_6$-alkenyl)-N—($C_1$-$C_6$-alkoxy)aminocarbonyl, N—($C_3$-$C_6$-alkynyl)-N—($C_1$-$C_6$-alkoxy)aminocarbonyl, ($C_1$-$C_6$-alkyl)aminothiocarbonyl, di($C_1$-$C_6$-alkyl)aminothiocarbonyl or $C_1$-$C_6$-alkylcarbonyl-$C_1$-$C_6$-alkyl,
where the alkyl, cycloalkyl and alkoxy radicals mentioned may be partially or fully halogenated and/or may bear from one to three of the following groups: cyano, hydroxyl, $C_1$-$C_4$-alkyl, $C_3$-$C_6$-cycloalkyl, $C_1$-$C_6$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-alkylthio, amino, $C_1$-$C_4$-alkylamino, di($C_1$-$C_4$-alkyl)amino, $C_1$-$C_4$-alkylcarbonylamino, hydroxycarbonyl, $C_1$-$C_4$-alkoxycarbonyl, aminocarbonyl, $C_1$-$C_4$-alkylaminocarbonyl, di($C_1$-$C_4$-alkyl)amino-carbonyl or $C_1$-$C_4$-alkylcarbonyloxy;
aryl, aryl-$C_1$-$C_4$-alkyl, aryl-$C_2$-$C_4$-alkenyl, aryl-$C_2$-$C_4$-alkynyl, aryl-$C_1$-$C_4$-haloalkyl, aryl-$C_2$-$C_4$-haloalkenyl, aryl-$C_3$-$C_4$-haloalkynyl, aryl-$C_1$-$C_4$-hydroxyalkyl, arylcarbonyl-$C_1$-$C_4$-alkyl, aryl-$C_1$-$C_4$-alkylcarbonyl-$C_1$-$C_4$-alkyl, arylcarbonyloxy-$C_1$-$C_4$-alkyl, aryloxycarbonyl-$C_1$-$C_4$-alkyl, aryloxy-$C_1$-$C_4$-alkyl, arylamino-$C_1$-$C_4$-alkyl, arylthio-$C_1$-$C_4$-alkyl, arylsulfinyl-$C_1$-$C_4$-alkyl, arylsulfonyl-$C_1$-$C_4$-alkyl, heterocyclyl, heterocyclyl-$C_1$-$C_4$-alkyl, heterocyclyl-$C_2$-$C_4$-alkenyl, heterocyclyl-$C_2$-$C_4$-alkynyl, heterocyclyl-$C_1$-$C_4$-haloalkyl, heterocyclyl-$C_2$-$C_4$-haloalkenyl, heterocyclyl-$C_3$-$C_4$-haloalkynyl, heterocyclyl-$C_1$-$C_4$-hydroxyalkyl, heterocyclylcarbonyl-$C_1$-$C_4$-alkyl, heterocyclyl-$C_1$-$C_4$-alkyl-carbonyl-$C_1$-$C_4$-alkyl, heterocyclylcarbonyloxy-$C_1$-$C_4$-alkyl, heterocyclyloxycarbonyl-$C_1$-$C_4$-alkyl, heterocyclyloxy-$C_1$-$C_4$-alkyl, heterocyclylamino-$C_1$-$C_4$-alkyl, heterocyclylthio-$C_1$-$C_4$-alkyl, heterocyclylsulfinyl-$C_1$-$C_4$-alkyl, heterocyclylsulfonyl-$C_1$-$C_4$-alkyl, where the aforementioned radicals may be partially or fully halogenated and/or may bear from one to three radicals from the group of cyano, nitro, $C_1$-$C_6$-alkyl, $C_1$-$C_6$-haloalkyl, hydroxyl, $C_1$-$C_6$-hydroxyalkyl, hydroxycarbonyl-$C_1$-$C_6$-alkyl, $C_1$-$C_6$-alkoxycarbonyl-$C_1$-$C_6$-alkyl, $C_1$-$C_6$-alkoxy, $C_1$-$C_6$-haloalkoxy, hydroxycarbonyl, $C_1$-$C_6$-alkoxycarbonyl, aminocarbonyl, ($C_1$-$C_6$-alkyl)aminocarbonyl, di($C_1$-$C_6$-alkyl)aminocarbonyl, hydroxycarbonyl-$C_1$-$C_6$-alkoxy, $C_1$-$C_6$-alkoxycarbonyl-$C_1$-$C_6$-alkoxy, amino, $C_1$-$C_6$-alkylamino, di($C_1$-$C_6$-alkyl)amino, $C_1$-$C_6$-alkylsulfonylamino, $C_1$-$C_6$-haloalkylsulfonylamino, ($C_1$-$C_6$-alkyl)aminocarbonylamino, di($C_1$-$C_6$-alkyl)-aminocarbonylamino, aryl and aryl($C_1$-$C_6$-alkyl);
where the $R^1$ and $R^2$ radicals are different than one another;
$R^3$ is $C_1$-$C_6$-alkyl;
$R^4$ is aryl which may be partially or fully halogenated and/or may bear from one to three radicals from the group of cyano, nitro, $C_1$-$C_6$-alkyl, $C_1$-$C_6$-haloalkyl, hydroxyl, $C_1$-$C_6$-hydroxyalkyl, $C_1$-$C_6$-alkoxy, $C_1$-$C_6$-haloalkoxy, hydroxycarbonyl, $C_1$-$C_6$-alkoxycarbonyl, $C_1$-$C_6$-alkylamino, di($C_1$-$C_6$-alkyl)amino, aryl and aryl($C_1$-$C_6$-alkyl); and
* represents the S or R configuration, and
** represents the S and/or R configuration;
by converting the imine of the formula I in the presence of hydrogen and a heterogeneous copper-containing catalyst.

There are frequent descriptions in the literature of the diastereoselective conversion of chiral imines, the substituent on the imino nitrogen bearing the chirality, in the presence of hydrogen, to give corresponding amines in the presence of platinum oxide, palladium on carbon, etc. EP 443 606 describes the reaction of optically active 1-phenylethylamine with 4-(4-methoxyphenyl)-2-butanone and subsequent hydrogenation with hydrogen in the presence of palladium on carbon (Example 4).

It is also known that diastereoselective hydrogenations of imines, the substituent on the imino nitrogen bearing the chirality, to corresponding amines can be carried out in the presence of nickel skeletal catalysts (Raney™ type). EP 443 606 likewise describes the reaction of optically active 1-phenylethylamine with 4-(4-methoxyphenyl)-2-butanone and subsequent hydrogenation with hydrogen in the presence of Raney nickel (Example 1B).

A disadvantage in these processes is the sometimes poor diastereoselectivity of the hydrogenation and/or the difficulty in removing the nickel skeletal catalyst (Raney™ type).

WO 01/09080 further describes a process for cis-selective preparation of cyclic amines of the sertraline type, by reacting a cyclic ketone with an achiral amine to the corresponding imine and the latter is then subjected to a catalytic hydrogenation in the presence of a copper-containing catalyst, especially copper chromite.

It was an object of the present invention to provide a generally applicable process for diastereoselective conversion of chiral imines, the substituent on the imino nitrogen thus bearing the chirality, to corresponding amines, which does not have the abovementioned disadvantages.

In accordance with the above object, it has been found that the diastereoselectivity and/or the conversion in the reaction of chiral imines of the formula I to amines of the formula II can be improved when heterogeneous catalysts which comprise nickel, cobalt and/or zinc, and which additionally comprise copper, are used.

The process according to the invention proceeds from chiral imines of the formula I, wherein the substituent on the imino nitrogen (—C*HR³R⁴) is either in the R or S configuration.

The reaction is effected generally in a solvent. However, it is also possible to carry out the reaction in substance, especially when the imine of the formula I is liquid at the reaction temperature. The solvents used are solvents which are inert under the reaction conditions, such as alcohols, for example methanol, ethanol, n-propanol, isopropanol, cyclopentanol, cyclohexanol, ethylene glycol, propylene glycol etc., aromatic hydrocarbons, for example benzene, toluene, ethylbenzene, xylene etc., chlorinated hydrocarbons, for example methylene chloride, chloroform, carbon tetrachloride, 1,2-dichloromethane, chlorobenzene etc., ethers, for example diethyl ether, methyl tert-butyl ether, ethylene glycol dimethyl ether, tetrahydrofuran, dioxane, dipolar aprotic solvents, for example N-methylpyrrolidone, dimethyl sulfoxide, sulfolane, dimethylformamide, dimethylacetamide etc., or mixtures thereof. Preference is given to performing the reaction in an alcohol, such as methanol, ethanol, n-propanol, isopropanol, cyclopentanol, cyclohexanol, ethylene glycol, propylene glycol etc., preferably methanol, ethanol or isopropanol, or an aromatic hydrocarbon, such as benzene, toluene, ethylbenzene, xylene etc., preferably toluene or ethylbenzene, or mixtures thereof.

The weight ratio of imine to solvent may vary within wide ranges. Typically, it is within the range from 0.01% to 99%, preferably from 0.1% to 95%, especially from 1% to 90%, more preferably from 10% to 70%, exceptionally preferably from 15-60%.

Typically, the reaction is performed at a temperature from room temperature to reflux temperature of the reaction mixture, generally from room temperature to 200° C.

In general, the reaction is performed at a pressure of from standard pressure to 200 bar, preferably from 40 to 150 bar, especially from 50 to 100 bar. It is possible to increase the pressure up to the desired pressure in stages or else continuously.

The hydrogen or the hydrogen of the hydrogen-comprising gas stream can be reacted fully or partly. In the latter case, it may be advantageous from case to case to recycle this gas stream partly or fully, or to recirculate it. In the case that the copper-containing catalyst used is activated before the reaction, this gas stream can also be used for this purpose.

Typically, hydrogen of technical grade quality is used. The hydrogen can, though, also be used in the form of a hydrogen-comprising gas, i.e. as an admixture of an inert gas, such as nitrogen, helium, neon, argon or carbon dioxide, preferably nitrogen or argon.

The inventive reaction is carried out in the presence of a heterogeneous copper-containing catalyst.

This heterogeneous copper-containing catalyst preferably comprises, based on the total weight of the catalyst,
0.1-95% by weight of copper;
0.1-85% by weight of at least one metal selected from the group of nickel, cobalt and zinc;
0-15% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium;
where the sum of the percentages by weight does not exceed 100%.

In general, the heterogeneous copper-containing catalyst comprises a support material. Useful support materials include carbon, for example activated carbon, graphite or carbon black, or a porous metal oxide. Examples of suitable porous metal oxides are aluminum oxide, silicon dioxide, aluminosilicates, titanium dioxide, zirconium dioxide, magnesium oxide or mixtures thereof, preferably aluminum oxide, titanium dioxide or zirconium dioxide. However, it is also possible to use, as support materials, aluminum phosphates, mullites, kieselguhr, bauxites and potassium aluminates.

In particular, the total weight of the abovementioned catalytically active metals and if appropriate promoters in the heterogeneous copper-containing catalyst, based on its total weight, is at most 95% by weight, preferably at most 90% by weight.

In a further embodiment, this heterogeneous copper-containing catalyst is an unsupported catalyst.

In one embodiment, this heterogeneous copper-containing catalyst comprises, based on the total weight of the catalyst
1-90% by weight of copper;
0.1-80% by weight of at least one metal selected from the group of nickel, cobalt and zinc;
0-15% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

In particular, this heterogeneous copper-containing catalyst comprises, based on the total weight of the catalyst,
2-85% by weight of copper;
0.1-80% by weight of at least one metal selected from the group of nickel, cobalt and zinc;
0-15% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

In a further embodiment, this heterogeneous copper-containing catalyst comprises, based on the total weight of the catalyst,
2-50% by weight of copper;
0-30% by weight of at least one metal selected from the group of nickel and cobalt;
0.5-50% by weight of zinc;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

This heterogeneous copper-containing catalyst preferably comprises, based on the total weight of the catalyst,
5-40% by weight of copper;
0-30% by weight of at least one metal selected from the group of nickel and cobalt;
5-50% by weight of zinc;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

In particular, this heterogeneous copper-containing catalyst comprises, based on the total weight of the catalyst,
10-35% by weight of copper;

0-30% by weight of at least one metal selected from the group of nickel and cobalt;
10-45% by weight of zinc;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

This heterogeneous copper-containing catalyst more preferably comprises, based on the total weight of the catalyst,
10-35% by weight of copper;
10-40% by weight of zinc;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

This copper-containing catalyst especially preferably comprises, as catalytically active metals, only copper and zinc, especially in each case (but independently) from 5 to 50% by weight, more preferably from 10 to 45% by weight, especially preferably from 20 to 40% by weight, based on the total weight of the catalyst. The support material is preferably a porous metal oxide, especially aluminum oxide, titanium dioxide or zirconium dioxide.

In a further embodiment, this heterogeneous copper-containing catalyst comprises, based on the total weight of the catalyst,
2-50% by weight of copper;
0.1-70% by weight of nickel;
0-30% by weight of at least one metal selected from the group of cobalt and zinc;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

This heterogeneous copper-containing catalyst preferably comprises, based on the total weight of the catalyst,
2-40% by weight of copper;
1-65% by weight of nickel;
0-10% by weight of at least one metal selected from the group of cobalt and zinc;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

In particular, this heterogeneous copper-containing catalyst comprises, based on the total weight of the catalyst,
2-25% by weight of copper;
3-60% by weight of nickel;
0-10% by weight of at least one metal selected from the group of cobalt and zinc;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

This heterogeneous copper-containing catalyst more preferably comprises, based on the total weight of the catalyst,
2-25% by weight of copper;
3-50% by weight of nickel;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium, preferably molybdenum.

This copper-containing catalyst preferably comprises, as catalytically active metals, only copper and nickel, especially in each case (but independently) from 2 to 15% by weight, more preferably from 2 to 10% by weight, especially preferably from 3 to 8% by weight, based on the total weight of the catalyst. The support material is preferably a porous metal oxide, especially aluminum oxide, titanium dioxide or zirconium dioxide.

Equally preferably, this copper-containing catalyst comprises, as catalytically active metals or promoters, only copper, nickel and molybdenum, especially from 2 to 25% by weight of copper, from 20 to 60% by weight of nickel, from 0.01 to 5% by weight of molybdenum, more preferably from 5 to 20% by weight of copper, from 30 to 50% by weight of nickel, from 0.1 to 2% by weight of molybdenum, especially preferably from 10 to 15% by weight of copper, from 35 to 45% by weight of nickel, from 0.5 to 1.5% by weight of molybdenum, based on the total weight of the catalyst. The support material is preferably a porous metal oxide, especially aluminum oxide, titanium dioxide or zirconium dioxide.

In a further embodiment, this heterogeneous copper-containing catalyst comprises, based on the total weight of the catalyst,
2-40% by weight of copper;
0.1-80% by weight of at least one metal selected from the group of nickel and cobalt;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

This heterogeneous copper-containing catalyst preferably comprises, based on the total weight of the catalyst,
2-40% by weight of copper;
0.1-40% by weight of nickel;
0.1-40% by weight of cobalt;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

This heterogeneous copper-containing catalyst especially comprises, based on the total weight of the catalyst,
2-30% by weight of copper;
0.5-35% by weight of nickel;
0.5-35% by weight of cobalt;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

This heterogeneous copper-containing catalyst more preferably comprises, based on the total weight of the catalyst,
2-20% by weight of copper;
1-30% by weight of nickel;

1-30% by weight of cobalt;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium, preferably molybdenum.

This copper-containing catalyst preferably comprises, as catalytically active metals, only copper, nickel and cobalt, especially from 2 to 25% by weight of copper and in each case independently from 1 to 35% by weight of nickel and/or cobalt, more preferably from 2 to 20% by weight of copper and in each case independently from 10 to 30% by weight of nickel and/or cobalt, especially preferably from 5 to 15% by weight of copper and in each case independently from 15 to 25% by weight of nickel and/or cobalt, based on the total weight of the catalyst. The support material is preferably a porous metal oxide, especially aluminum oxide, titanium dioxide or zirconium dioxide.

Equally especially, this copper-containing catalyst comprises, as catalytically active metals, only copper, nickel and cobalt, more preferably from 2 to 10% by weight of copper and in each case independently from 1 to 10% by weight of nickel and/or cobalt, especially preferably from 2 to 5% by weight of copper and in each case independently from 2 to 5% by weight of nickel and/or cobalt, based on the total weight of the catalyst. The support material is preferably a porous metal oxide, especially aluminum oxide, titanium dioxide or zirconium dioxide.

In a further embodiment, this heterogeneous copper-containing catalyst comprises, based on the total weight of the catalyst,
2-40% by weight of copper;
0.1-80% by weight of cobalt;
0-15% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

In particular, this heterogeneous copper-containing catalyst comprises, based on the total weight of the catalyst,
2-20% by weight of copper;
2-20% by weight of cobalt;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

This heterogeneous copper-containing catalyst more preferably comprises, based on the total weight of the catalyst,
2-15% by weight of copper;
2-15% by weight of cobalt;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

This copper-containing catalyst preferably comprises, as catalytically active metals, only copper and cobalt, especially in each case (but independently) from 2 to 15% by weight, more preferably from 3 to 10% by weight, especially preferably from 3 to 8% by weight, based on the total weight of the catalyst. The support material is preferably a porous metal oxide, especially aluminum oxide, titanium dioxide or zirconium dioxide.

In a further embodiment, this heterogeneous copper-containing catalyst comprises, based on the total weight of the catalyst,
5-40% by weight of copper;
20-80% by weight of cobalt;
0-15% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

This heterogeneous copper-containing catalyst more preferably comprises, based on the total weight of the catalyst,
10-25% by weight of copper;
40-70% by weight of cobalt;
0.1-15% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium, preferably molybdenum, manganese and phosphorus.

This copper-containing catalyst preferably comprises, as catalytically active metals or promoters, only copper, cobalt, molybdenum and manganese, especially from 5 to 40% by weight of copper, from 30 to 80% by weight of cobalt and in each case independently from 0.1 to 15% by weight of molybdenum, manganese and phosphorus, more preferably from 10 to 35% by weight of copper, from 40 to 75% by weight of cobalt and in each case independently from 0.5 to 15% by weight of molybdenum, manganese and phosphorus, especially preferably from 12 to 25% by weight of copper, from 45 to 60% by weight of cobalt and in each case independently from 0.5 to 15% by weight of molybdenum, manganese and phosphorus, based on the total weight of the catalyst. In a particular embodiment, this catalyst is an unsupported catalyst.

The catalyst typically has a BET surface area (determined to DIN 66131) of from 50 up to 150 m$^2$/g, preferably from 70 to 130 m$^2$/g, especially from 75 to 120 m$^2$/g. In general, the pore volume of the catalyst (determined by means of Hg porosimetry to DIN 66133) is from 0.1 to 0.4 ml/g, preferably from 0.15 to 0.35 ml/g, especially from 0.15 to 0.3 ml/g.

The catalyst can, however, also be prepared by customary processes (A. Farkas, in Ullmann's Encyclopedia of Industrial Chemistry, Electronic Release 2000, chapters 5.3, 5.4, 5.6 to 5.10).

For example, it is possible to prepare the support from corresponding compounds which are converted to the oxide of the particular support on calcination. For this purpose, especially hydroxides, carbonates and carboxylates are suitable. The oxide or the corresponding precursor which is converted to the oxide of the particular support on calcination can be prepared by processes known per se, for example by the sol-gel process, by precipitation, dewatering of the corresponding carboxylates, dry mixing, slurrying or spray drying. In precipitation, typically soluble salts of aluminum, titanium, zirconium etc. are used, for example the corresponding halides, preferably chloride, alkoxides, nitrate etc., preferably nitrates of aluminum, titanium, zirconium etc. In addition, it is possible to incorporate stabilizers into the support by customary methods.

It is likewise possible to incorporate assistants into the support, which facilitate the shaping of the support, for example graphite or stearic acid. This is followed by the shaping. In general, extrudates, tablets, spheres, spall, monoliths etc., are prepared by the customary methods.

The calcination is effected typically with air or a mixture of air and nitrogen, at a temperature of from 300 to 800° C., preferably at from 500 to 600° C. It may be advantageous to add water vapor to the air or to the air/nitrogen mixture.

It is now possible to apply the inventive catalytically active metals and/or promoters to the support. Typically, the support is impregnated with a solution of a corresponding metal precursor or promoter precursor or saturated therein. The impregnation can be effected by the incipient wetness method, wherein the porous volume of the support is filled up by about the same volume of impregnation solution and—if appropriate after maturation—the support is dried; or an excess of solution is employed, in which case the volume of this solution is greater than the porous volume of the support. In this case, the support is mixed with the impregnation solution and stirred for a sufficiently long period. The excess impregnation solution is shaken off, centrifuged off or removed by filtration. From case to case, the addition of acids, neutral salts or bases may also facilitate the impregnation/saturation. Thorough impregnation of the support can be achieved from case to case by, for example, heating the solution during the impregnation/saturation, adding surface-active substances or evacuating the support. In addition, it is possible to spray the support with a solution of the appropriate precursor. In this case, the appropriate support is treated with a solution of the appropriate metal precursor and/or promoter precursor, which is such that the support absorbs the solution.

However, other preparation methods known to those skilled in the art, for example chemical vapor deposition, sol impregnation etc., are also possible.

Suitable metal precursors and/or promoter precursors are corresponding soluble metal salts, including halides, especially chloride, nitrate, acetate, alkaline carbonates, formate, oxalate, citrate, tartrate.

The metal and/or promoter precursors can be applied together or successively by the aforementioned methods. It may also be advantageous to comply with a certain sequence here.

However, other preparation methods known to those skilled in the art, for example chemical vapor deposition, sol impregnation etc., are also possible.

The support to which the inventive catalytically active metal precursors are applied is now calcined. The calcination is effected typically with air or a mixture of air and nitrogen, at a temperature of from 300 to 800° C., preferably at from 400 to 600° C. It may be advantageous to add water vapor to the air or to the air/nitrogen mixture.

After the calcination, the heterogeneous copper-containing catalyst is appropriately conditioned, whether by adjusting it to a particular particle size by grinding or by mixing it with shaping assistants such as graphite or stearic acid after it has been ground, pressed to pressings by means of a tableting press and heat-treated. The heat treatment temperatures correspond generally to the temperatures in the calcination.

However, it is also possible to prepare the heterogeneous copper-containing catalysts by employing precipitation methods. For example, they can be obtained by a coprecipitation of the metal and/or promoter precursors from an aqueous salt solution comprising these metals/promoters by means of mineral bases in the presence of a slurry of a sparingly soluble, oxygen-containing support precursor compound or of the support itself, and subsequent washing, drying and calcination of the resulting precipitate.

The sparingly soluble, oxygen-containing support precursor compounds or supports themselves used may, for example, be oxides, oxyhydrates, phosphates, borates and silicates, for example oxides, oxyhydrates, phosphates, borates and silicates, for example zirconium dioxide, zirconium oxide hydrate, zirconium phosphates, borates and silicates, silicon dioxide, aluminum oxide, aluminum oxyhydrate, titanium dioxide, and further compounds which are suitable for this purpose and are known to those skilled in the art. The slurries of the sparingly soluble support precursor compounds or supports themselves can be prepared by suspending fine powders of these support precursor compounds or supports themselves in water with vigorous stirring. Advantageously, these slurries are prepared by precipitating the sparingly soluble support precursor compounds from aqueous salt solutions by means of mineral bases.

In particular, the inventive heterogeneous copper-containing catalysts are prepared by means of a coprecipitation of all of their components. To this end, an aqueous salt solution comprising the catalyst components, under hot conditions and with stirring, is admixed with an aqueous mineral base, especially an alkali metal base—for example sodium carbonate, sodium hydroxide, potassium carbonate or potassium hydroxide—until the precipitation is complete. The type of salts used is generally not critical—since the principal factor in this procedure is the water solubility of the salts, a criterion is their good water solubility, which is required to prepare these comparatively highly concentrated salt solutions. It is considered to be obvious that, when selecting the salts of the individual components, of course, only salts with those anions which do not lead to disruption, whether by causing undesired precipitation or by complicating or preventing precipitation by complex formation, are selected.

The precipitates obtained in these precipitation reactions are generally chemically inhomogeneous and consist, inter alia, of mixtures of the oxides, oxide hydrates, hydroxides, carbonates and insoluble and basic salts of the metals/promoters used. It may be found to be favorable for the filterability of the precipitates if they are aged, i.e. if they are left alone for a certain time after precipitation, if appropriate under hot conditions or while passing air through.

The precipitates obtained by these precipitation reactions are processed further as usual to give the inventive heterogeneous copper-containing catalysts. After washing, they are generally dried at from 80 to 200° C., preferably at from 100 to 150° C., and then calcined. The calcination (heat treatment) is generally performed at temperatures between 300 and 800° C., preferably at from 400 to 600° C., especially at from 450 to 550° C.

After the calcination, the heterogeneous copper-containing catalyst is appropriately conditioned, whether by adjusting it to a particular particle size by grinding or by mixing it with shaping assistants such as graphite or stearic acid after it has been ground, pressed to pressings by means of a tableting press and heat-treated. The heat treatment temperatures correspond generally to the temperatures in the calcination.

The heterogeneous copper-containing catalysts obtained in this way comprise the catalytically active metals/promoters in the form of a mixture of their oxygen compounds, i.e. especially as the oxides and mixed oxides. The heterogeneous copper-containing catalysts obtained in this way can be stored as such.

The catalyst thus obtained can be activated before use in the diaselective hydrogenation of compounds of the formula I. To this end, it is treated with hydrogen or a mixture of hydrogen and nitrogen at temperatures of from 100 to 300° C. In this case, it may be advantageous to begin with a low hydrogen fraction in the hydrogen/nitrogen mixture and to increase the hydrogen fraction continuously or in stages in the course of the activation process. The prereduction can be carried out, for example, first at from 150 to 200° C. over a period of from 12 to 20 hours in a nitrogen/hydrogen atmosphere, and then continued for another approx. 24 hours at from 200 to 300° C. in a hydrogen atmosphere.

The activation of the catalyst is generally carried out in the reactor in which the inventive hydrogenation is to be effected. However, it is also possible to undertake the activation of the catalyst before installation into the reactor in question.

Typically, the catalyst is used in reduced form in the inventive hydrogenation. In this context, it may be advantageous to activate the catalyst present in reduced form once again. To this end, it is treated with hydrogen or a mixture of hydrogen and an inert gas, e.g. nitrogen, at temperatures of from room temperature to 300° C., preferably at from 150 to 300° C., and a hydrogen pressure of from 10 to 60 bar, preferably at max. 50 bar. In this context, it may be advantageous to activate with hydrogen without inert gas. However, it may also be advantageous to activate with a mixture of hydrogen and inert gas, in which case to begin with the hydrogen/inert gas mixture and to increase the hydrogen fraction continuously in the course of the activation process.

However, it is also possible to use the catalyst, in its oxidic form or else in its reduced form, in the diaselective hydrogenation of imines of the formula I without any further prior activation.

The process according to the invention can be performed batchwise, semicontinuously or continuously.

In a batchwise procedure, the reaction mixture is worked up by customary methods, for example by removing the catalyst, for example by filtration, allowing it to settle and removing the liquid phase or by centrifugation, and the solvent is removed from the filtrate, supernatant or centrifugate thus obtained, for example, by distilling it off. The inventive hydrogenation is carried out in the hydrogenation reactors known to those skilled in the art. Examples thereof include so-called slurry reactors, trickle-bed reactors and bubble columns (P. N. Rylander, Ullmann's Encyclopedia, Electronic Release 2007, chapter: Hydrogenation and Dehydrogenation, p. 2-3).

In general, the hydrogenation of the imines of the formula I will proceed in the liquid phase, for example in a stirred autoclave, a bubble column, a circulation reactor, for instance a loop reactor or a fixed bed reactor. The fixed bed reactor can be operated either in liquid phase mode or in trickle mode.

However, it is also possible, especially when the imine of the formula I exhibits a certain degree of volatility, to perform the hydrogenation without solvent in the gas phase. Examples of suitable reactors for this purpose are fixed bed reactors or fluidized bed reactors.

The reaction output can be worked up and purified by the customary methods. Examples of useful methods for this purpose are distillation, liquid extraction and/or crystallization.

The compounds of the formula II obtained by the process according to the invention have a diastereomeric ratio of >0.70, preferably >0.9, especially >0.95, exceptionally preferably of >0.98 (where the diastereomeric ratio is the molar ratio of desired diastereomer:undesired diastereomer). If it is desirable to achieve an even higher diastereomeric ratio, the diastereomeric ratio of the compounds of the formula II obtained by the process according to the invention can be increased by known methods, for example recrystallization.

The diastereomeric ratio can be determined by customary methods known to those skilled in the art; typically, it is determined indirectly via the rotation or directly by means of gas or liquid chromatography. The determination can be effected directly or via appropriate derivatives of the target compound.

The catalyst can be reused in the process according to the invention.

The compounds of the formula I are known or can be prepared by literature methods.

For example, it is possible to obtain the compounds of the formula I by reacting ketones of the formula III with amines of the formula IV, where the $R^1$ to $R^4$ radicals are each as defined for the compounds of the formula I.

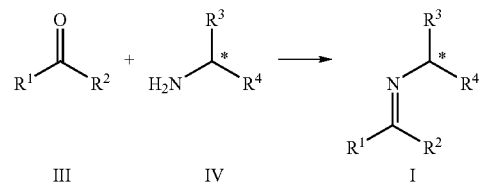

Typically, the ketone of the formula III and the amine of the formula IV are used in stoichiometric amounts. From case to case, it may also be advantageous to use one or the other reactant in excess. In general, the reaction is carried out in a solvent. Suitable solvents are inert solvents, for example alcohols, ethers, hydrocarbons, halogenated hydrocarbons etc., especially those which form an azeotrope with water, for example toluene or ethylbenzene, thus allowing the water formed in the reaction to be removed. When one of the reactants used forms an azeotropic mixture with water, this reactant can be used in excess, and the water formed can be removed azeotropically. This can be done in the presence or in the absence of an additional solvent. In addition, it may be advantageous from case to case to add catalytic amounts of acid, for example p-toluenesulfonic acid. The reaction can also be carried out in the presence of heterogeneous catalysts, for example aluminum oxides, titanium dioxide, zirconium dioxide, silicon oxides, or clay minerals such as montmorillonite.

From case to case, it may also be advantageous to scavenge the water released in the reaction with a molecular sieve. Alternatively, it may also be advantageous to distill off the water formed in the reaction. The reaction takes place typically at a temperature from room temperature to reflux temperature of the reaction mixture. The reaction mixture is worked up by the methods known to those skilled in the art.

In the abovementioned reaction, instead of the chiral amine of the formula IV, it is also possible to use a corresponding racemate. On completion of reaction and if appropriate workup, a racemate separation can be carried out by the methods known to those skilled in the art.

The compounds of the formula I can also be obtained by reacting an alkyne of the formula V with an amine of the formula IV.

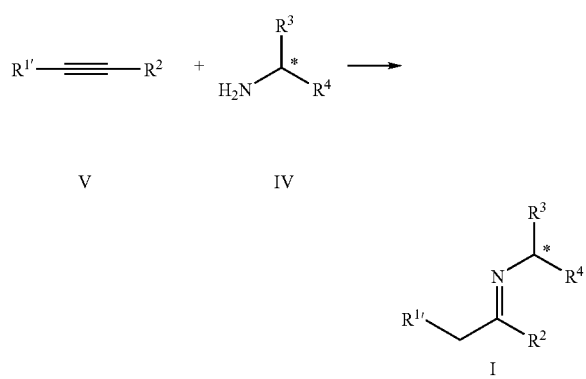

The definitions of the $R^2$ to $R^4$ radicals correspond to those specified for the compounds of the formula I. And $R^{1'}$—$CH_2$ represents the definitions of $R^1$ which are compatible therewith. The same applies to $R^{1'}$.

Typically, the alkyne of the formula V and the amine of the formula IV are used in a stoichiometric ratio. However, it may be advantageous to use the alkyne of the formula V in excess. The reaction is generally carried out in an inert solvent, for example an ether, a hydrocarbon, a halogenated hydrocarbon etc., or mixtures thereof, at from room temperature to reflux temperature of the reaction mixture. In general, the reaction is carried out at standard pressure. From case to case, however, it may also be advantageous to carry out the reaction at elevated pressure, preferably in the range from 10 to 200 bar. Completion of reaction is followed by workup by the methods known to those skilled in the art.

In the abovementioned reaction, instead of the chiral amine of the formula IV, it is also possible to use a corresponding racemate. On completion of reaction and if appropriate workup, a racemate separation can be carried out by the methods known to those skilled in the art.

It is equally possible to prepare the imines of the formula I by reacting nitroso compounds of the formula VII with phosphorus ylides of the formula VI.

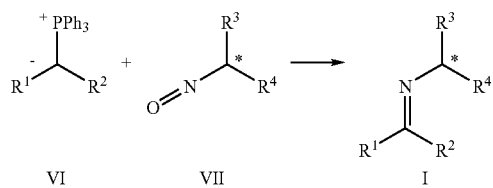

The $R^1$ to $R^4$ radicals are each as defined under the compounds of the formula I.

Typically, the phosphorus ylide of the formula VI and the nitroso compound of the formula VII are used in a stoichiometric ratio. From case to case, however, it may also be advantageous to use one or the other reaction component in excess or in deficiency. The reaction is generally carried out in an inert solvent, for example an ether, a hydrocarbon, a halogenated hydrocarbon etc., or mixtures thereof, at from room temperature to reflux temperature of the reaction mixture. In general, the reaction is carried out at standard pressure. Completion of reaction is followed by workup by the methods known to those skilled in the art.

In the abovementioned reaction, instead of the chiral nitroso compound of the formula VII, it is also possible to use a corresponding racemate. On completion of reaction and if appropriate workup, a racemate separation can be carried out by the methods known to those skilled in the art.

The preparation of the imines of the formula I can be carried out continuously, semicontinuously or batchwise.

Preference is given to using, in the process according to the invention, imines of the formula I, or amines of the formula II, where the radicals are each independently defined as follows:

$R^1$, $R^2$ are each $C_1$-$C_6$-alkyl, $C_3$-$C_6$-cycloalkyl, $C_2$-$C_6$-alkenyl, $C_2$-$C_6$-alkynyl, $C_2$-$C_6$-haloalkenyl, $C_2$-$C_6$-haloalkynyl or $C_1$-$C_6$-alkylcarbonyl-$C_1$-$C_6$-alkyl, where the alkyl, cycloalkyl and alkoxy radicals mentioned may be partially or fully halogenated and/or may bear from one to three of the following groups: cyano, hydroxyl, $C_1$-$C_4$-alkyl, $C_3$-$C_6$-cycloalkyl, $C_1$-$C_6$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-alkylthio, amino, $C_1$-$C_4$-alkylamino, di($C_1$-$C_4$-alkyl)amino;

aryl, aryl-$C_1$-$C_4$-alkyl, aryl-$C_2$-$C_4$-alkenyl, aryl-$C_2$-$C_4$-alkynyl, aryl-$C_1$-$C_4$-haloalkyl, aryl-$C_2$-$C_4$-haloalkenyl, aryl-$C_3$-$C_4$-haloalkynyl, aryl-$C_1$-$C_4$-hydroxyalkyl, arylcarbonyl-$C_1$-$C_4$-alkyl, aryl-$C_1$-$C_4$-alkylcarbonyl-$C_1$-$C_4$-alkyl, aryloxy-$C_1$-$C_4$-alkyl, arylamino-$C_1$-$C_4$-alkyl, arylthio-$C_1$-$C_4$-alkyl, arylsulfinyl-$C_1$-$C_4$-alkyl, arylsulfonyl-$C_1$-$C_4$-alkyl, heterocyclyl, heterocyclyl-$C_1$-$C_4$-alkyl, heterocyclyl-$C_2$-$C_4$-alkenyl, heterocyclyl-$C_2$-$C_4$-alkynyl, heterocyclyl-$C_1$-$C_4$-haloalkyl, heterocyclyl-$C_2$-$C_4$-haloalkenyl, heterocyclyl-$C_3$-$C_4$-haloalkynyl, heterocyclyl-$C_1$-$C_4$-hydroxyalkyl, heterocyclylcarbonyl-$C_1$-$C_4$-alkyl, heterocyclyl-$C_1$-$C_4$-alkylcarbonyl-$C_1$-$C_4$-alkyl, heterocyclyloxy-$C_1$-$C_4$-alkyl, heterocyclylamino-$C_1$-$C_4$-alkyl, heterocyclylthio-$C_1$-$C_4$-alkyl, heterocyclylsulfinyl-$C_1$-$C_4$-alkyl, heterocyclylsulfonyl-$C_1$-$C_4$-alkyl, where the aforementioned radicals may be partially or fully halogenated and/or may bear from one to three radicals from the group of cyano, nitro, $C_1$-$C_6$-alkyl, $C_1$-$C_6$-haloalkyl, hydroxyl, $C_1$-$C_6$-hydroxyalkyl, $C_1$-$C_6$-alkoxy, $C_1$-$C_6$-haloalkoxy, $C_1$-$C_6$-alkoxycarbonyl, di($C_1$-$C_6$-alkyl)aminocarbonyl, amino, $C_1$-$C_6$-alkylamino, di($C_1$-$C_6$-alkyl)amino, $C_1$-$C_6$-alkylsulfonylamino, $C_1$-$C_6$-haloalkylsulfonylamino, aryl and aryl($C_1$-$C_6$-alkyl);

$R^3$ is $C_1$-$C_4$-alkyl, preferably methyl; and $R^4$ is aryl which may be partially or fully halogenated and/or may bear from one to three radicals from the group of cyano, nitro, $C_1$-$C_6$-alkyl, $C_1$-$C_6$-haloalkyl, $C_1$-$C_6$-alkoxy, $C_1$-$C_6$-haloalkoxy, aryl and aryl($C_1$-$C_6$-alkyl); preferably phenyl or 1-naphthyl;

In particular, in the process according to the invention, imines of the formula I are used, or amines of the formula II are prepared, where the radicals are each independently defined as follows:

$R^1$, $R^2$ are each $C_1$-$C_6$-alkyl or $C_3$-$C_6$-cycloalkyl, where the alkyl or cycloalkyl radicals mentioned may be partially or fully halogenated and/or may bear from one to three of the following groups: cyano, hydroxyl, $C_3$-$C_6$-cycloalkyl, $C_1$-$C_6$-alkoxy-$C_1$-$C_4$-alkyl, $C_1$-$C_4$-alkoxy-$C_1$-$C_4$-alkoxy- $C_1$-$C_4$-alkyl, $C_1$-$C_4$-alkoxy, $C_1$-$C_4$-alkylthio, amino, $C_1$-$C_4$-alkylamino, di($C_1$-$C_4$-alkyl)amino, $C_1$-$C_4$-alkylcarbonylamino, hydroxycarbonyl, $C_1$-$C_4$-alkoxycarbonyl, aminocarbonyl, $C_1$-$C_4$-alkylaminocarbonyl, di($C_1$-$C_4$-alkyl)aminocarbonyl or $C_1$-$C_4$-alkylcarbonyloxy; especially $C_1$-$C_6$-alkyl or $C_3$-$C_6$-cycloalkyl, where the alkyl or cycloalkyl radicals mentioned may be partially or fully halogenated and/or may bear one of the following groups: cyano, $C_1$-$C_4$-alkoxy, $C_1$-$C_4$-alkylthio, di($C_1$-$C_4$-alkyl)amino, $C_1$-$C_4$-alkoxycarbonyl, di($C_1$-$C_4$-alkyl)aminocarbonyl or $C_1$-$C_4$-alkylcarbonyloxy; likewise especially $C_1$-$C_6$-alkyl or $C_3$-$C_6$-cycloalkyl, where the alkyl or cycloalkyl radicals mentioned may be partially or fully halogenated and/or may bear from one to three of the following groups: cyano, $C_1$-$C_4$-alkoxycarbonyl, di($C_1$-$C_4$-alkyl)aminocarbonyl or $C_1$-$C_4$-alkylcarbonyloxy;

more preferably $C_1$-$C_6$-alkyl, where the alkyl radical mentioned may be partially or fully halogenated and/or may bear from one to three of the following groups: cyano, di($C_1$-$C_4$-alkyl)amino, $C_1$-$C_4$-alkoxycarbonyl, di($C_1$-$C_4$-alkyl)aminocarbonyl or $C_1$-$C_4$-alkylcarbonyloxy; exceptionally preferably $C_1$-$C_6$-alkyl;

phenyl, phenyl-$C_1$-$C_4$-alkyl, phenyl-$C_2$-$C_4$-alkenyl, phenyl-$C_2$-$C_4$-alkynyl, phenyl-$C_1$-$C_4$-haloalkyl, phenyl-$C_2$-$C_4$-haloalkenyl, phenyl-$C_3$-$C_4$-haloalkynyl, phenyl-$C_1$-$C_4$-hydroxyalkyl, phenylcarbonyl-$C_1$-$C_4$-alkyl, phenyl-$C_1$-$C_4$-alkylcarbonyl-$C_1$-$C_4$-alkyl, phenylcarbonyloxy-$C_1$-$C_4$-alkyl, phenyloxycarbonyl-$C_1$-$C_4$-alkyl, phenyloxy-$C_1$-$C_4$-alkyl, phenylamino-$C_1$-$C_4$-alkyl, phenylthio-$C_1$-$C_4$-alkyl, phenylsulfinyl-$C_1$-$C_4$-alkyl, phenylsulfonyl-$C_1$-$C_4$-alkyl, heterocyclyl, heterocyclyl-$C_1$-$C_4$-alkyl, heterocyclyl-$C_2$-$C_4$-alkenyl, heterocyclyl-$C_2$-$C_4$-alkynyl, heterocyclyl-$C_1$-$C_4$-haloalkyl, heterocyclyl-$C_2$-$C_4$-haloalkenyl, heterocyclyl-$C_3$-$C_4$-haloalkynyl, heterocyclyl-$C_1$-$C_4$-hydroxyalkyl, heterocyclylcarbonyl-$C_1$-$C_4$-alkyl, heterocyclyl-$C_1$-$C_4$-alkylcarbonyl-$C_1$-$C_4$-alkyl, heterocyclylcarbonyloxy-$C_1$-$C_4$-alkyl, heterocyclyloxycarbonyl-$C_1$-$C_4$-alkyl, heterocyclyloxy-$C_1$-$C_4$-alkyl, heterocyclylamino-$C_1$-$C_4$-alkyl, heterocyclylthio-$C_1$-$C_4$-alkyl, heterocyclylsulfinyl-$C_1$-$C_4$-alkyl, heterocyclylsulfonyl-$C_1$-$C_4$-alkyl, where the aforementioned radicals may be partially or fully halogenated and/or may bear from one to three radicals from the group of cyano, nitro, $C_1$-$C_6$-alkyl, $C_1$-$C_6$-haloalkyl, hydroxyl, $C_1$-$C_6$-hydroxyalkyl, $C_1$-$C_6$-alkoxy, $C_1$-$C_6$-haloalkoxy, hydroxycarbonyl, $C_1$-$C_6$-alkoxycarbonyl, aminocarbonyl, ($C_1$-$C_6$-alkyl)amino-carbonyl, di($C_1$-$C_6$-alkyl)aminocarbonyl, hydroxycarbonyl-$C_1$-$C_6$-alkoxy, $C_1$-$C_6$-alkoxycarbonyl-$C_1$-$C_6$-alkoxy, amino, $C_1$-$C_6$-alkylamino, di($C_1$-$C_6$-alkyl)amino, $C_1$-$C_6$-alkylsulfonylamino, $C_1$-$C_6$-haloalkylsulfonylamino, ($C_1$-$C_6$-alkyl)amino-carbonylamino, di($C_1$-$C_6$-alkyl)aminocarbonylamino, aryl and aryl($C_1$-$C_6$-alkyl); especially phenyl, phenyl-$C_1$-$C_4$-alkyl, phenyl-$C_2$-$C_4$-alkenyl, phenyl-$C_1$-$C_4$-haloalkyl, phenyl-$C_1$-$C_4$-hydroxyalkyl, phenylcarbonyl-$C_1$-$C_4$-alkyl, phenyl-$C_1$-$C_4$-alkylcarbonyl-$C_1$-$C_4$-alkyl, phenylcarbonyloxy-$C_1$-$C_4$-alkyl, phenyloxycarbonyl-$C_1$-$C_4$-alkyl, phenyloxy-$C_1$-$C_4$-alkyl, phenylamino-$C_1$-$C_4$-alkyl, phenylthio-$C_1$-$C_4$-alkyl, phenylsulfonyl-$C_1$-$C_4$-alkyl, heterocyclyl, heterocyclyl-$C_1$-$C_4$-alkyl, heterocyclyl-$C_2$-$C_4$-alkenyl, heterocyclyl-$C_1$-$C_4$-haloalkyl, heterocyclyl-$C_1$-$C_4$-hydroxyalkyl, heterocyclylcarbonyl-$C_1$-$C_4$-alkyl, heterocyclyl-$C_1$-$C_4$-alkylcarbonyl-$C_1$-$C_4$-alkyl, heterocyclylcarbonyloxy-$C_1$-$C_4$-alkyl, heterocyclyloxycarbonyl-$C_1$-$C_4$-alkyl, heterocyclyloxy-$C_1$-$C_4$-alkyl, heterocyclylamino-$C_1$-$C_4$-alkyl, heterocyclylthio-$C_1$-$C_4$-alkyl, heterocyclylsulfonyl-$C_1$-$C_4$-alkyl, where the aforementioned radicals may be partially or fully halogenated and/or may bear from one to three radicals from the group of cyano, nitro, $C_1$-$C_6$-alkyl, $C_1$-$C_6$-haloalkyl, hydroxyl, $C_1$-$C_6$-hydroxyalkyl, $C_1$-$C_6$-alkoxy, $C_1$-$C_6$-haloalkoxy, hydroxycarbonyl, $C_1$-$C_6$-alkoxycarbonyl, aminocarbonyl, ($C_1$-$C_6$-alkyl)aminocarbonyl, di($C_1$-$C_6$-alkyl)aminocarbonyl, hydroxycarbonyl-$C_1$-$C_6$-alkoxy, di($C_1$-$C_6$-alkyl)amino, di($C_1$-$C_6$-alkyl)aminocarbonylamino, aryl and aryl($C_1$-$C_6$-alkyl); more preferably phenyl, phenyl-$C_1$-$C_4$-alkyl, phenyl-$C_1$-$C_4$-haloalkyl, phenylcarbonyloxy-$C_1$-$C_4$-alkyl, phenyloxycarbonyl-$C_1$-$C_4$-alkyl, phenyloxy-$C_1$-$C_4$-alkyl, heterocyclyl, heterocyclyl-$C_1$-$C_4$-alkyl, heterocyclyl-$C_1$-$C_4$-haloalkyl, heterocyclylcarbonyloxy-$C_1$-$C_4$-alkyl, heterocyclyloxycarbonyl-$C_1$-$C_4$-alkyl, heterocyclyloxy-$C_1$-$C_4$-alkyl, where the aforementioned radicals may be partially or fully halogenated and/or may bear from one to three radicals from the group of cyano, $C_1$-$C_6$-alkyl, $C_1$-$C_6$-haloalkyl, $C_1$-$C_6$-alkoxy, $C_1$-$C_6$-haloalkoxy, hydroxycarbonyl, $C_1$-$C_6$-alkoxy-carbonyl, aminocarbonyl, ($C_1$-$C_6$-alkyl) aminocarbonyl, di($C_1$-$C_6$-alkyl)-aminocarbonyl, di($C_1$-$C_6$-alkyl)amino, aryl and aryl($C_1$-$C_6$-alkyl);

$R^3$ is $C_1$-$C_4$-alkyl, preferably methyl; and $R^4$ is aryl which may be partially or fully halogenated and/or may bear from one to three radicals from the group of cyano, nitro, $C_1$-$C_6$-alkyl, $C_1$-$C_6$-haloalkyl, $C_1$-$C_6$-alkoxy, $C_1$-$C_6$-haloalkoxy, aryl and aryl($C_1$-$C_6$-alkyl); preferably phenyl or 1-naphthyl.

Particular preference is given, in the process according to the invention, to using imines of the formula I, or to preparing amines of the formula II, where the radicals are each independently defined as follows:

$R^1$, $R^2$ are each $C_1$-$C_6$-alkyl or $C_3$-$C_6$-cycloalkyl, where the alkyl or cycloalkyl radicals mentioned may be partially or fully halogenated and/or may bear from one to three of the following groups: cyano, hydroxyl, $C_3$-$C_6$-cycloalkyl, $C_1$-$C_6$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-alkylthio, amino, $C_1$-$C_4$-alkylamino, di($C_1$-$C_4$-alkyl)amino, $C_1$-$C_4$-alkylcarbonylamino, hydroxycarbonyl, $C_1$-$C_4$-alkoxycarbonyl, aminocarbonyl, $C_1$-$C_4$-alkylaminocarbonyl, di($C_1$-$C_4$-alkyl)aminocarbonyl or $C_1$-$C_4$-alkylcarbonyloxy; especially $C_1$-$C_6$-alkyl or $C_3$-$C_6$-cycloalkyl, where the alkyl or cycloalkyl radicals mentioned may be partially or fully halogenated and/or may bear one of the following groups: cyano, $C_1$-$C_4$-alkoxy, $C_1$-$C_4$-alkylthio, di($C_1$-$C_4$-alkyl)amino, $C_1$-$C_4$-alkoxycarbonyl, di($C_1$-$C_4$-alkyl)aminocarbonyl or $C_1$-$C_4$-alkylcarbonyloxy; likewise especially $C_1$-$C_6$-alkyl or $C_3$-$C_6$-cycloalkyl, where the alkyl or cycloalkyl radicals mentioned may be partially or fully halogenated and/or may bear from one to three of the following groups: cyano, $C_1$-$C_4$-alkoxycarbonyl, di($C_1$-$C_4$-alkyl)aminocarbonyl or $C_1$-$C_4$-alkylcarbonyloxy;

more preferably $C_1$-$C_6$-alkyl, where the alkyl radical mentioned may be partially or fully halogenated and/or may bear from one to three of the following groups: cyano, di($C_1$-$C_4$-alkyl)amino, $C_1$-$C_4$-alkoxycarbonyl, di($C_1$-$C_4$-alkyl)aminocarbonyl or $C_1$-$C_4$-alkylcarbonyloxy;

exceptionally preferably $C_1$-$C_6$-alkyl;

$R^3$ is $C_1$-$C_4$-alkyl, preferably methyl; and $R^4$ is aryl which may be partially or fully halogenated and/or may bear from one to three radicals from the group of cyano, nitro, $C_1$-$C_6$-alkyl, $C_1$-$C_6$-haloalkyl, $C_1$-$C_6$-alkoxy, $C_1$-$C_6$-haloalkoxy, aryl and aryl($C_1$-$C_6$-alkyl);

preferably phenyl or 1-naphthyl which may be partially or fully halogenated and/or may bear from one to three radicals from the group of cyano, nitro, $C_1$-$C_6$-alkyl, $C_1$-$C_6$-haloalkyl, $C_1$-$C_6$-$C_1$-$C_6$-alkoxy, $C_1$-$C_6$-haloalkoxy, aryl and aryl($C_1$-$C_6$-alkyl);

especially phenyl or 1-naphthyl.

Particular preference is likewise given, in the process according to the invention, to using imines of the formula I, or to preparing amines of the formula II, where the radicals are each independently defined as follows:

$R^1$ is $C_1$-$C_6$-alkyl or $C_3$-$C_6$-cycloalkyl, where the alkyl or cycloalkyl radicals mentioned may be partially or fully halogenated and/or may bear from one to three of the following groups: cyano, hydroxyl, $C_3$-$C_6$-cycloalkyl, $C_1$-$C_6$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-alkylthio, amino, $C_1$-$C_4$-alkylamino, di($C_1$-$C_4$-alkyl)amino, $C_1$-$C_4$-alkylcarbonylamino, hydroxycarbonyl, $C_1$-$C_4$-alkoxycarbonyl, aminocarbonyl, $C_1$-$C_4$-alkyl-aminocarbonyl, di($C_1$-$C_4$-alkyl)aminocarbonyl or $C_1$-$C_4$-alkylcarbonyloxy; especially $C_1$-$C_6$-alkyl or $C_3$-$C_6$-cycloalkyl, where the alkyl or cycloalkyl radicals mentioned may be partially or fully halogenated and/or may bear one of the following groups: cyano, $C_1$-$C_4$-alkoxy, $C_1$-$C_4$-alkylthio, di($C_1$-$C_4$-alkyl)amino, $C_1$-$C_4$-alkoxycarbonyl, di($C_1$-$C_4$-alkyl)aminocarbonyl or $C_1$-$C_4$-alkylcarbonyloxy; likewise especially $C_1$-$C_6$-alkyl or $C_3$-$C_6$-cycloalkyl, where the alkyl or cycloalkyl radicals mentioned may be partially or fully halogenated and/or may bear from one to three of the following groups: cyano, $C_1$-$C_4$-alkoxycarbonyl, di($C_1$-$C_4$-alkyl)aminocarbonyl or $C_1$-$C_4$-alkylcarbonyloxy;

more preferably $C_1$-$C_6$-alkyl, where the alkyl radical mentioned may be partially or fully halogenated and/or may bear from one to three of the following groups: cyano, di($C_1$-$C_4$-alkyl)amino, $C_1$-$C_4$-alkoxycarbonyl, di($C_1$-$C_4$-alkyl)aminocarbonyl or $C_1$-$C_4$-alkylcarbonyloxy;

exceptionally preferably $C_1$-$C_6$-alkyl;

$R^2$ is aryl, aryl-$C_1$-$C_4$-alkyl, aryl-$C_2$-$C_4$-alkenyl, aryl-$C_2$-$C_4$-alkynyl, aryl-$C_1$-$C_4$-haloalkyl, aryl-$C_2$-$C_4$-haloalkenyl, aryl-$C_3$-$C_4$-haloalkynyl, aryl-$C_1$-$C_4$-hydroxyalkyl, arylcarbonyl-$C_1$-$C_4$-alkyl, aryl-$C_1$-$C_4$-alkylcarbonyl-$C_1$-$C_4$-alkyl, arylcarbonyloxy-$C_1$-$C_4$-alkyl, aryloxycarbonyl-$C_1$-$C_4$-alkyl, aryloxy-$C_1$-$C_4$-alkyl, arylamino-$C_1$-$C_4$-alkyl, arylthio-$C_1$-$C_4$-alkyl, arylsulfinyl-$C_1$-$C_4$-alkyl, arylsulfonyl-$C_1$-$C_4$-alkyl, heterocyclyl, heterocyclyl-$C_1$-$C_4$-alkyl, heterocyclyl-$C_2$-$C_4$-alkenyl, heterocyclyl-$C_2$-$C_4$-alkynyl, heterocyclyl-$C_1$-$C_4$-haloalkyl, heterocyclyl-$C_2$-$C_4$-haloalkenyl, heterocyclyl-$C_3$-$C_4$-haloalkynyl, heterocyclyl-$C_1$-$C_4$-hydroxyalkyl, heterocyclyl carbonyl-$C_1$-$C_4$-alkyl, heterocyclyl-$C_1$-$C_4$-alkylcarbonyl-$C_1$-$C_4$-alkyl, heterocyclylcarbonyloxy-$C_1$-$C_4$-alkyl, heterocyclyloxycarbonyl-$C_1$-$C_4$-alkyl, heterocyclyloxy-$C_1$-$C_4$-alkyl, heterocyclylamino-$C_1$-$C_4$-alkyl, heterocyclylthio-$C_1$-$C_4$-alkyl, heterocyclylsulfinyl-$C_1$-$C_4$-alkyl, heterocyclylsulfonyl-$C_1$-$C_4$-alkyl, where the aforementioned radicals may be partially or fully halogenated and/or may bear from one to three radicals from the group of cyano, nitro, $C_1$-$C_6$-alkyl, $C_1$-$C_6$-haloalkyl, hydroxyl, $C_1$-$C_6$-hydroxyalkyl, hydroxycarbonyl-$C_1$-$C_6$-alkyl, $C_1$-$C_6$-alkoxycarbonyl-$C_1$-$C_6$-alkyl, $C_1$-$C_6$-alkoxy, $C_1$-$C_6$-haloalkoxy, hydroxycarbonyl, $C_1$-$C_6$-alkoxycarbonyl, aminocarbonyl, ($C_1$-$C_6$-alkyl)aminocarbonyl, di($C_1$-$C_6$-alkyl)aminocarbonyl, hydroxycarbonyl-$C_1$-$C_6$-alkoxy, $C_1$-$C_6$-alkoxycarbonyl-$C_1$-$C_6$-alkoxy, amino, $C_1$-$C_6$-alkylamino, di($C_1$-$C_6$-alkyl)amino, $C_1$-$C_6$-alkylsulfonylamino, $C_1$-$C_6$-haloalkylsulfonylamino, ($C_1$-$C_6$-alkyl)aminocarbonylamino, di($C_1$-$C_6$-alkyl)-aminocarbonylamino, aryl and aryl($C_1$-$C_6$-alkyl);

preferably phenyl, phenyl-$C_1$-$C_4$-alkyl, phenyl-$C_2$-$C_4$-alkenyl, phenyl-$C_2$-$C_4$-alkynyl, phenyl-$C_1$-$C_4$-haloalkyl, phenyl-$C_2$-$C_4$-haloalkenyl, phenyl-$C_3$-$C_4$-haloalkynyl, phenyl-$C_1$-$C_4$-hydroxyalkyl, phenylcarbonyl-$C_1$-$C_4$-alkyl, phenyl-$C_1$-$C_4$-alkylcarbonyl-$C_1$-$C_4$-alkyl, phenylcarbonyloxy-$C_1$-$C_4$-alkyl, phenyloxycarbonyl-$C_1$-$C_4$-alkyl, phenyloxy-$C_1$-$C_4$-alkyl, phenylamino-$C_1$-$C_4$-alkyl, phenylthio-$C_1$-$C_4$-alkyl, phenylsulfinyl-$C_1$-$C_4$-alkyl, phenylsulfonyl-$C_1$-$C_4$-alkyl, heterocyclyl, heterocyclyl-$C_1$-$C_4$-alkyl, heterocyclyl-$C_2$-$C_4$-alkenyl, heterocyclyl-$C_2$-$C_4$-alkynyl, heterocyclyl-$C_1$-$C_4$-haloalkyl, heterocyclyl-$C_2$-$C_4$-haloalkenyl, heterocyclyl-$C_3$-$C_4$-haloalkynyl, heterocyclyl-$C_1$-$C_4$-hydroxyalkyl, heterocyclyl-carbonyl-$C_1$-$C_4$-alkyl, heterocyclyl-$C_1$-$C_4$-alkylcarbonyl-$C_1$-$C_4$-alkyl, heterocyclylcarbonyloxy-$C_1$-$C_4$-alkyl, heterocyclyloxycarbonyl-$C_1$-$C_4$-alkyl, heterocyclyloxy-$C_1$-$C_4$-alkyl, heterocyclylamino-$C_1$-$C_4$-alkyl, heterocyclylthio-$C_1$-$C_4$-alkyl, heterocyclylsulfinyl-$C_1$-$C_4$-alkyl, heterocyclylsulfonyl-$C_1$-$C_4$-alkyl, where the aforementioned radicals may be partially or fully halogenated and/or may bear from one to three radicals from the group of cyano, nitro, $C_1$-$C_6$-alkyl, $C_1$-$C_6$-haloalkyl, hydroxyl, $C_1$-$C_6$-hydroxyalkyl, $C_1$-$C_6$-alkoxy, $C_1$-$C_6$-haloalkoxy, hydroxycarbonyl, $C_1$-$C_6$-alkoxycarbonyl, aminocarbonyl, ($C_1$-$C_6$-alkyl)amino-carbonyl, di($C_1$-$C_6$-alkyl)aminocarbonyl, hydroxycarbonyl-$C_1$-$C_6$-alkoxy, $C_1$-$C_6$-alkoxycarbonyl-$C_1$-$C_6$-alkoxy, amino, $C_1$-$C_6$-alkylamino, di($C_1$-$C_6$-alkyl)amino, $C_1$-$C_6$-alkylsulfonylamino, $C_1$-$C_6$-haloalkylsulfonylamino, ($C_1$-$C_6$-alkyl)amino-carbonylamino, di($C_1$-$C_6$-alkyl)aminocarbonylamino, aryl and aryl($C_1$-$C_6$-alkyl);

especially phenyl, phenyl-$C_1$-$C_4$-alkyl, phenyl-$C_2$-$C_4$-alkenyl, phenyl-$C_1$-$C_4$-haloalkyl, phenyl-$C_1$-$C_4$-hydroxyalkyl, phenylcarbonyl-$C_1$-$C_4$-alkyl, phenyl-$C_1$-$C_4$-alkylcarbonyl-$C_1$-$C_4$-alkyl, phenylcarbonyloxy-$C_1$-$C_4$-alkyl, phenyloxycarbonyl-$C_1$-$C_4$-alkyl, phenyloxy-$C_1$-$C_4$-alkyl, phenylamino-$C_1$-$C_4$-alkyl, phenylthio-$C_1$-$C_4$-alkyl, phenylsulfonyl-$C_1$-$C_4$-alkyl, heterocyclyl, heterocyclyl-$C_1$-$C_4$-alkyl, heterocyclyl-$C_2$-$C_4$-alkenyl, heterocyclyl-$C_1$-$C_4$-haloalkyl, heterocyclyl-$C_1$-$C_4$-hydroxyalkyl, heterocyclylcarbonyl-$C_1$-$C_4$-alkyl, heterocyclyl-$C_1$-$C_4$-alkylcarbonyl-$C_1$-$C_4$-alkyl, heterocyclylcarbonyloxy-$C_1$-$C_4$-alkyl, heterocycyloxycarbonyl-$C_1$-$C_4$-alkyl, heterocyclyloxy-$C_1$-$C_4$-alkyl, heterocyclylamino-$C_1$-$C_4$-alkyl, heterocyclylthio-$C_1$-$C_4$-alkyl, heterocyclylsulfonyl-$C_1$-$C_4$-alkyl, where the aforementioned radicals may be partially or fully halogenated and/or may bear from one to three radicals from the group of cyano, nitro, $C_1$-$C_6$-alkyl, $C_1$-$C_6$-haloalkyl, hydroxyl, $C_1$-$C_6$-hydroxyalkyl, $C_1$-$C_6$-alkoxy, $C_1$-$C_6$-haloalkoxy, hydroxycarbonyl, $C_1$-$C_6$-alkoxycarbonyl, aminocarbonyl, ($C_1$-$C_6$-alkyl)aminocarbonyl, di($C_1$-$C_6$-alkyl)aminocarbonyl, hydroxycarbonyl-$C_1$-$C_6$-alkoxy, di($C_1$-$C_6$-alkyl)amino, di($C_1$-$C_6$-alkyl)aminocarbonylamino, aryl and aryl($C_1$-$C_6$-alkyl);

more preferably phenyl, phenyl-$C_1$-$C_4$-alkyl, phenyl-$C_1$-$C_4$-haloalkyl, phenylcarbonyloxy-$C_1$-$C_4$-alkyl, phenyloxycarbonyl-$C_1$-$C_4$-alkyl, phenyloxy-$C_1$-$C_4$-alkyl, heterocyclyl, heterocyclyl-$C_1$-$C_4$-alkyl, heterocyclyl-$C_1$-$C_4$-haloalkyl, heterocyclylcarbonyloxy-$C_1$-$C_4$-alkyl, heterocyclyloxycarbonyl-$C_1$-$C_4$-alkyl, heterocyclyloxy-$C_1$-$C_4$-alkyl, where the aforementioned radicals may be partially or fully halogenated and/or may bear from one to three radicals from the group of cyano, $C_1$-$C_6$-haloalkyl, $C_1$-$C_6$-alkoxy, $C_1$-$C_6$-haloalkoxy, hydroxycarbonyl, $C_1$-$C_6$-alkoxy-carbonyl, di($C_1$-$C_6$-alkyl)amino, aryl and aryl ($C_1$-$C_6$-alkyl);

$R^3$ is $C_1$-$C_4$-alkyl, preferably methyl; and $R^4$ is aryl which may be partially or fully halogenated and/or may bear from one to three radicals from the group of cyano, nitro, $C_1$-$C_6$-alkyl, $C_1$-$C_6$-haloalkyl, $C_1$-$C_6$-alkoxy, $C_1$-$C_6$-haloalkoxy, aryl and aryl($C_1$-$C_6$-alkyl); preferably phenyl or 1-naphthyl.

The amines of the formula II can be cleaved hydrogenolytically to the chiral amines of the formula VIII

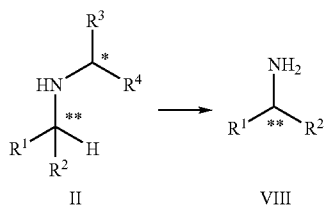

where the $R^1$ and $R^2$ radicals are each as defined for the compounds of the formula I, by processes known per se.

Typically, this hydrogenolysis is carried out in an inert solvent, for example an alcohol, such as methanol, ethanol, isopropanol or butanol, an ether, for example tetrahydrofuran, dioxane, a hydrocarbon, for example benzene, toluene, ethylbenzene or xylene, or mixtures thereof. The hydrogenolysis can be carried out by means of hydrogen in the presence of a catalytic amount of a platinum group metal element, preferably over Pt/C, Pd/C or Pd/$Al_2O_3$, more preferably over Pd/C or Pd/$Al_2O_3$. In this case, the hydrogen is generally used in excess. The reaction is effected generally at from room temperature to reflux temperature of the reaction mixture and from standard pressure up to a pressure of 200 bar. After the reaction has ended, the reaction mixture is worked up by methods known to those skilled in the art.

However, it is also possible to carry out the hydrogenolysis by means of metal hydrides, for example lithium aluminum hydride, sodium boranate, sodium cyanoboranate, diborane etc. In this case, the reactants are generally used in a stoichiometric ratio. From case to case, it may also be advantageous to use metal hydride in excess. The reaction is effected generally at from room temperature to reflux temperature of the reaction mixture, at standard pressure. After the reaction has ended, the reaction mixture is worked up by methods known to those skilled in the art.

The hydrogenolysis of the amines of the formula II can be carried out continuously, semicontinuously or batchwise.

The $R^1$ and $R^2$ radicals of the compounds of the formula I, II, III, VI and VIII and the $R^{1'}$ radical of the compounds of the formula V may, according to the substitution pattern, bear further chiral centers. These compounds too fall within the subject matter of the present invention.

The organic molecular moieties specified for the substituents $R^1$-$R^4$ or as radicals on phenyl, aryl, heteroaryl or heterocyclyl rings etc. constitute collective terms for individual lists of the specific group members.

All hydrocarbon chains may be straight or branched.

Unless stated otherwise, halogenated substituents bear preferably from one to five identical or different heteroatoms. The definition "halogen" in each case represents fluorine, chlorine, bromine or iodine.

Examples of further definitions are:

aryl: mono- to tricyclic aromatic carbocycle having from 6 to 14 ring members, for example phenyl, naphthyl and anthracenyl, preferably phenyl, naphthyl;

heterocyclyl: monocyclic, saturated or partially unsaturated hydrocarbons which have from three to six ring members and, as well as carbon atoms, may comprise from one to four nitrogen atoms, or from one to three nitrogen atoms and one oxygen or sulfur atom, or from one to three oxygen atoms, or from one to three sulfur atoms, and which may be bonded via a carbon atom or a nitrogen atom, for example.

e.g. 2-oxiranyl, 2-oxetanyl, 3-oxetanyl, 2-aziridinyl, 3-thiethanyl, 1-azetidinyl, 2-azetidinyl, e.g. 2-tetrahydrofuranyl, 3-tetrahydrofuranyl, 2-tetrahydrothienyl, 3-tetra-hydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 1,2,3,4-tetrazolidin-5-yl;

e.g. 1-pyrrolidinyl, 2-isothiazolidinyl, 2-isothiazolidinyl, 1-pyrazolidinyl, 3-oxazolidinyl, 3-thiazolidinyl, 1-imidazolidinyl, 1,2,4-triazolidin-1-yl, 1,2,4-oxadiazolidin- 2-yl, 1,2,4-oxadiazolidin-4-yl, 1,2,4-thiadiazolidin-2-yl, 1,2,4-thiadiazolidin-4-yl, 1,2,3,4-tetrazolidin-1-yl, e.g. 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 4,5-dihydropyrrol-2-yl, 4,5-dihydropyrrol-3-yl, 2,5-dihydropyrrol-2-yl, 2,5-dihydropyrrol-3-yl, 4,5-dihydroisoxazol-3-yl, 2,5-dihydroisoxazol-3-yl, 2,3-di-hydroisoxazol-3-yl, 4,5-dihydroisoxazol-4-yl, 2,5-dihydroisoxazol-4-yl, 2,3-dihydro-isoxazol-4-yl, 4,5-dihydroisoxazol-5-yl, 2,5-dihydroisoxazol-5-yl, 2,3-dihydro-isoxazol-5-yl, 4,5-dihydroisothiazol-3-yl, 2,5-dihydroisothiazol-3-yl, 2,3-dihydro-isothiazol-3-yl, 4,5-dihydroisothiazol-4-yl, 2,5-dihydroisothiazol-4-yl, 2,3-dihydro-isothiazol-4-yl, 4,5-dihydroisothiazol-5-yl, 2,5-dihydroisothiazol-5-yl, 2,3-dihydro-isothiazol-5-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-3-yl, 3,4-dihydropyrazol-4-yl, 3,4-dihydropyrazol-5-yl, 4,5-dihydropyrazol-3-yl, 4,5-dihydropyrazol-4-yl, 4,5-dihydropyrazol-5-yl, 2,3-dihydroimidazol-2-yl, 2,3-dihydroimidazol-3-yl, 2,3-di-hydroimidazol-4-yl, 2,3-dihydroimidazol-5-yl, 4,5-dihydroimidazol-2-yl, 4,5-di-hydroimidazol-4-yl, 4,5-dihydroimidazol-5-yl, 2,5-dihydroimidazol-2-yl, 2,5-di-hydroimidazol-4-yl, 2,5-dihydroimidazol-5-yl, 2,3-dihydrooxazol-3-yl, 2,3-dihydro-oxazol-4-yl, 2,3-dihydrooxazol-5-yl, 3,4-dihydrooxazol-3-yl, 3,4-dihydrooxazol-4-yl, 3,4-dihydrooxazol-5-yl, 2,3-dihydrothiazol-3-yl, 2,3-dihydrothiazol-4-yl, 2,3-di-hydrothiazol-5-yl, 3,4-dihydrothiazol-3-yl, 3,4-dihydrothiazol-4-yl, 3,4-dihydrothiazol-5-yl, 3,4-dihydrothiazol-2-yl, 3,4-dihydrothiazol-3-yl, 3,4-dihydrothiazol-4-yl, e.g. 4,5-dihydropyrrol-1-yl, 2,5-dihydropyrrol-1-yl, 4,5-dihydroisoxazol-2-yl, 2,3-dihydroisoxazol-1-yl, 4,5-di-hydroisothiazol-2-yl, 2,3-dihydroisothiazol-1-yl, 2,3-di-hydropyrazol-1-yl, 4,5-dihydropyrazol-1-yl, 3,4-dihydropyrazol-1-yl, 2,3-dihydro-imidazol-1-yl, 4,5-dihydroimidazol-1-yl, 2,5-dihydroimidazol-1-yl, 2,3-dihydrooxazol-2-yl, 3,4-dihydrooxazol-2-yl, 2,3-dihydrothiazol-2-yl, 3,4-dihydrothiazol-2-yl;

e.g. 2-piperidinyl, 3-piperidinyl, 4-piperidinyl, 1,3-dioxan-2-yl, 1,3-dioxan-4-yl, 1,3-dioxan-5-yl, 1,4-dioxan-2-yl, 1,3-dithian-2-yl, 1,4-dithian-3-yl, 1,3-dithian-4-yl, 1,4-dithian-2-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexa-hydrotriazin-2-yl, 1,2,4-hexahydrotriazin-3-yl, tetrahydro-1,3-oxazin-2-yl, tetrahydro-1,3-oxazin-6-yl, 2-morpholinyl, 3-morpholinyl, 1,3,5-trioxan-2-yl;

e.g. 1-piperidinyl, 1-hexahydropyridazinyl, 1-hexahydropyrimidinyl, 1-piperazinyl, 1,3,5-hexahydrotriazin-1-yl, 1,2,4-hexahydrotriazin-1-yl, tetrahydro-1,3-oxazin-1-yl, 1-morpholinyl;

e.g. 2H-pyran-2-yl, 2H-pyran-3-yl, 2H-pyran-4-yl, 2H-pyran-5-yl, 2H-pyran-6-yl, 3,6-dihydro-2H-pyran-2-yl, 3,6-dihydro-2H-pyran-3-yl, 3,6-dihydro-2H-pyran-4-yl, 3,6-dihydro-2H-pyran-5-yl, 3,6-dihydro-2H-pyran-6-yl, 3,4-dihydro-2H-pyran-3-yl, 3,4-dihydro-2H-pyran-4-yl, 3,4-dihydro-2H-pyran-6-yl, 2H-thiopyran-2-yl, 2H-thiopyran-3-yl, 2H-thiopyran-4-yl, 2H-thiopyran-5-yl, 2H-thiopyran-6-yl, 5,6-dihydro-4H-1,3-oxazin-2-yl;

and heteroaryl.

Heteroaryl: mono- or bicyclic aromatic heteroaryl which has from 5 to 10 ring members and, as well as carbon atoms, comprises from 1 to 4 nitrogen atoms, or from 1 to 3 nitrogen atoms and one oxygen or one sulfur atom, or one oxygen or one sulfur atom, e.g. monocycles such as furyl (e.g. 2-furyl, 3-furyl), thienyl (e.g. 2-thienyl, 3-thienyl), pyrrolyl (e.g. pyrrol-2-yl, pyrrol-3-yl), pyrazolyl (e.g. pyrazol-3-yl, pyrazol-4-yl), isoxazolyl (e.g. isoxazol-3-yl, isoxazol-4-yl, isoxazol-5-yl), isothiazolyl (e.g. isothiazol-3-yl, isothiazol-4-yl, isothiazol-5-yl), imidazolyl (e.g. imidazol-2-yl, imidazol-4-yl), oxazolyl (e.g. oxazol-2-yl, oxazol-4-yl, oxazol-5-yl), thiazolyl (e.g. thiazol-2-yl, thiazol-4-yl, thiazol-5-yl), oxadiazolyl (e.g. 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl), thiadiazolyl (e.g. 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl), triazolyl (e.g. 1,2,3-triazol-4-yl, 1,2,4-triazol-3-yl), tetrazol-5-yl, pyridyl (e.g. pyridin-2-yl, pyridin-3-yl, pyridin-4-yl), pyrazinyl (e.g. pyridazin-3-yl, pyridazin-4-yl), pyrimidinyl (e.g. pyrimidin-2-yl, pyrimidin-4-yl, pyrimidin-5-yl), pyrazin-2-yl, triazinyl (e.g. 1,3,5-triazin-2-yl, 1,2,4-triazin-3-yl, 1,2,4-triazin-5-yl, 1,2,4-triazin-6-yl), tetrazinyl (e.g. 1,2,4,5-tetrazin-3-yl); and also bicycles such as the benzofused derivatives of the aforementioned monocycles, e.g. quinolinyl, isoquinolinyl, indolyl, benzothienyl, benzofuranyl, benzoxazolyl, benzothiazolyl, benzisothiazolyl, benzimidazolyl, benzopyrazolyl, benzothiadiazolyl, benzotriazolyl;

preferably 5- or 6-membered heteroaryl having from one to four nitrogen atoms, or from one to three nitrogen atoms and one oxygen or sulfur atom, or having one oxygen or sulfur atom:

e.g. aromatic 5-membered heterocyclic rings which are bonded via a carbon atom and, as well as carbon atoms, may comprise from one to four nitrogen atoms, or from one to three nitrogen atoms and one sulfur or oxygen atom, or one sulfur or oxygen atom as ring members, e.g. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

e.g. aromatic 6-membered heterocyclic rings which are bonded via a carbon atom and, as well as carbon atoms, may comprise from one to four, preferably from one to three nitrogen atoms as ring members, e.g. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

EXAMPLES

The copper-containing catalysts used in the examples which follow were prepared as described in the following documents:
DE 19826396, DE 4428004, EP 383132 and DE 3717111

The diastereomeric ratio of the compounds prepared in examples I and II which follow was determined as follows: derivatization with trifluoroacetic acid, gas chromatography separation on BGB 175 column.

The diastereomeric ratio of the compounds prepared in examples III and VI which follow was determined as follows: derivatization with trifluoroacetic acid, gas chromatography separation on Hydrodex beta 6-TBDM column.

The diastereomeric ratio of the compounds prepared in example VII which follows was determined as follows: gas chromatography separation on CP-SIL 19 CB column.

The diastereomeric ratio of the compounds prepared in example VIII which follows was determined as follows: gas chromatography separation on OV1701 column.

The diastereomeric ratio of the compounds prepared in example IX which follows was determined as follows: gas chromatography separation on RTX-5-Amine column.

I. General Method A

Diaselective hydrogenation of (R)-sec-butylidene(1-phenyl-ethyl)amine (Schiff base of (R)-(1-phenyl-ethyl)amine with 2-butanone)

540 mg of catalyst were introduced into a 15 ml autoclave and inertized with nitrogen. Subsequently, the catalyst was preactivated at a pressure of 50 bar at the temperature specified in table 1 with hydrogen for 2 hours. This was then followed by purging with nitrogen, cooling to room temperature at the same time, and then addition under nitrogen of a mixture of 5.97 ml of (R)-sec-butylidene(1-phenylethyl)amine and 1.03 ml of methanol. Subsequently, hydrogen was injected until a pressure of about 20 bar was attained and the reaction mixture was heated to 100° C. On attainment of this temperature, the pressure was increased to 70 bar with hydrogen and the stirrer was started at 1000 rpm. After 6 hours under these reaction conditions, a sample was taken and was analyzed by gas chromatography. The results are reported in table 1 below.

TABLE 1

| Example | Catalyst [metal loading in % by wt.] | Support | Activation [° C.] | Conversion [based on imine] | RR/RS ratio |
|---|---|---|---|---|---|
| 1.1 | Cu/Ni (5/5) | TiO$_2$ | 200 | 91 | 84/16 |
| 1.2 | Cu/Ni (5/5) | TiO$_2$ | 300 | >99 | 82/18 |
| 1.3 | Cu/Ni/Mo (13/40/1) | ZrO$_2$ | 200 | 99 | 85/15 |
| 1.4 | Cu/Co (5/5) | TiO$_2$ | 200 | >99 | 84/16 |
| 1.5 | Cu/Co (5/5) | TiO$_2$ | 300 | >99 | 84/16 |
| 1.6 | Cu/Ni/Co (3.3/3.3/3.3) | TiO$_2$ | 200 | 98 | 83/17 |
| 1.7 | Cu/Ni/Co (3.3/3.3/3.3) | TiO$_2$ | 300 | >99 | 85/15 |
| 1.8 | Cu/Ni/Co (11/21/21) | ZrO$_2$ | 200 | 99 | 85/15 |
| 1.9 | Cu/Zn (32/32) | Al$_2$O$_3$ | 200 | 98 | 83/17 |

For comparison, under the same conditions, the reaction was carried out with an unsupported iron catalyst (100% iron oxide), a copper on titanium dioxide catalyst, a nickel on titanium dioxide catalyst and a nickel/cobalt on titanium dioxide catalyst. The results are listed in table 2.

TABLE 2

Comparative examples

| Example | Catalyst [metal loading in % by wt.] | Support | Activation [° C.] | Conversion [based on imine] | RR/RS ratio |
|---|---|---|---|---|---|
| 2.1 | Fe | — | 200 | 10 | 59/41 |
| 2.2 | Cu (10) | TiO$_2$ | 200 | 23 | 76/24 |
| 2.3 | Cu (10) | TiO$_2$ | 300 | 21 | 78/22 |
| 2.4 | Ni (10) | TiO$_2$ | 200 | >99 | 75/25 |
| 2.5 | Co (10) | TiO$_2$ | 200 | 99 | 83/15 |
| 2.6 | Ni/Co (5/5) | TiO$_2$ | 200 | 90 | 77/23 |
| 2.7 | Ni/Co (5/5) | TiO$_2$ | 300 | >99 | 75/25 |

Comparison of the results from tables 1 and 2 shows clearly that the addition of copper to the particular non-copper-containing catalysts brings about an increase in the diastereoselectivity.

II. General Method B

Diaselective hydrogenation of (R)-sec-butylidene(1-phenyl-ethyl)amine (Schiff base of (R)-(1-phenyl-ethyl)amine with 2-butanone)

A mixture of (R)-sec-butylidene(1-phenylethyl)amine (imine); solvent and passivated catalyst, as specified in table 3, was initially charged in each case in a 300 ml autoclave. Subsequently, the mixture was inertized with nitrogen and heated to 100° C. Subsequently, at this temperature, hydrogen was injected up to the desired pressure, as likewise specified in each case in table 3, and, when the internal pressure declined, brought back to the desired pressure. After the run times specified in table 3 in each case, measured from injection of hydrogen, a sample was taken and was analyzed by gas chromatography. The results are reported in table 3 below.

TABLE 3

| Example | Imine [g] | Catalyst [metal loading in % by wt.] | Support | Cat.: imine [% by wt.] | Solvent | % by wt. of imine in solvent | p [bar] | Run time [h] | Conversion [based on imine] | RR/RS ratio |
|---|---|---|---|---|---|---|---|---|---|---|
| 3.1 | 41 | Cu/Ni/Co (3.3/3.3/3.3) | TiO$_2$ | 2.4 | methanol | 6 | 70 | 6 | 95 | 92/8 |
| 3.2 | 110 | Cu/Ni/Co (11/21/21) | ZrO$_2$ | 3 | ethyl-benzene | 60 | 70 | 12 | >99 | 91/9 |
| 3.3 | 110 | Cu/Ni/Co (11/21/21) | ZrO$_2$ | 3 | methanol | 60 | 70 | 12 | >99 | 91/9 |
| 3.4 | 110 | Cu/Ni/Mo (13/40/1) | ZrO$_2$ | 3 | ethyl-benzene | 60 | 70 | 12 | >99 | 91/9 |
| 3.5 | 110 | Cu/Ni/Mo (13/40/1) | ZrO$_2$ | 3 | methanol | 60 | 70 | 12 | >99 | 91/9 |
| 3.6 | 11 | Cu/Ni/Mo (13/40/1) | ZrO$_2$ | 1 | methanol | 8.5 | 100 | 24 | >99 | 91/9 |

For example, under the same conditions, the reaction was carried out with a Pt/C catalyst. The results are listed in table 4. The example shows that the inventive tests exhibit a higher diaselectivity.

TABLE 4

Comparative example

| Example | Imine [g] | Catalyst [metal loading in % by wt.] | Support | Cat.: imine [% by wt.] | Solvent | % by wt. of imine in solvent | p [bar] | Run time [h] | Conversion [based on imine] | RR/RS ratio |
|---|---|---|---|---|---|---|---|---|---|---|
| 4.1 | 11 | Pt (10) | C | 1 | methanol | 8.5 | 100 | 24 | >99 | 80/20 |

III. General Method C

Diaselective hydrogenation of (R)-1,2-dimethyl-propylidene(phenylethyl)amine (Schiff base of (R)-(1-phenylethyl)amine with 3-methyl-2-butanone)

540 mg of catalyst were added to a 15 ml autoclave and inertized with nitrogen. Subsequently, the catalyst was pre-activated with hydrogen at a pressure of 50 bar at the temperature specified in table 5 for 2 hours. This was then followed by purging with nitrogen, cooling to room temperature at the same time, and then addition under nitrogen of a mixture of 6.0 ml of (R)-1,2-dimethylpropylidene(1-phenylethyl)amine and 1.0 ml of ethylbenzene. Subsequently, hydrogen was injected until a pressure of about 20 bar was attained and the reaction mixture was heated to 100° C. On attainment of this temperature, the pressure was increased to 70 bar with hydrogen and the stirrer was started at 1000 rpm. After 3 hours under these reaction conditions, a sample was taken and was analyzed by gas chromatography. The results are reported in table 5 below.

TABLE 5

| Example | Catalyst [metal loading in %] | Support | Activation [° C.] | Conversion [based on imine] | RR/RS ratio |
|---|---|---|---|---|---|
| 5.1 | Cu/Ni (5/5) | TiO$_2$ | 200 | 72 | 94/6 |
| 5.2 | Cu/Ni/Mo (13/40/1) | ZrO$_2$ | 200 | >99 | 98/2 |
| 5.3 | Cu/Co (5/5) | TiO$_2$ | 200 | 80 | 98/2 |
| 5.4 | Cu/Co/Mn/Mo/P (20/50/7/3/3) | unsupported | 200 | 13 | 98/2 |
| 5.5 | Cu/Co/Mn/Mo/P (20/50/7/3/3) | unsupported | 300 | 20 | 98/2 |
| 5.6 | Cu/Ni/Co (3.3/3.3/3.3) | TiO$_2$ | 300 | 88 | 98/2 |
| 5.7 | Cu/Ni/Co (11/21/21) | ZrO$_2$ | 200 | 95 | 98/2 |
| 5.8 | Cu/Zn (32/32) | Al$_2$O$_3$ | 200 | 49 | 98/2 |

For comparison, under the same conditions, the reaction was carried out with an unsupported iron catalyst. The results are listed in table 6. All examples show that the inventive tests exhibit a higher diaselectivity.

TABLE 6

Comparative examples

| Example | Catalyst [metal loading in %] | Support | Activation [° C.] | Conversion [based on imine] | RR/RS ratio |
|---|---|---|---|---|---|
| 6.1 | Fe (10) | TiO$_2$ | 200 | 5 | 62/38 |
| 6.2 | Fe (10) | TiO$_2$ | 300 | 5 | 66/34 |
| 6.3 | Cu (10) | TiO$_2$ | 200 | 6 | 91/9 |
| 6.4 | Ni (10) | TiO$_2$ | 200 | 78 | 91/9 |

IV. General Method D

Diaselective hydrogenation of (R)-1,2-dimethyl-propylidene(phenylethyl)amine (Schiff base of (R)-(1-phenylethyl)amine with 3-methyl-2-butanone)

A mixture of (R)-1,2-dimethylpropylidene(1-phenylethyl)amine(imine), solvent and passivated catalyst, as specified in table 7, was initially charged in each case in an autoclave. Subsequently, the mixture was inertized with nitrogen and heated to the desired temperature. Subsequently, at this temperature, hydrogen was injected up to the desired pressure, as likewise specified in each case in table 7, and, when the internal pressure declined, brought back to the desired pressure. After the run times specified in table 7 in each case, measured from injection of hydrogen, a sample was taken and was analyzed by gas chromatography. The results are reported in table 7 below.

TABLE 7

| Example | Imine [g] | Catalyst [metal loading in %] | Support | Catalyst:imine [% by wt.] | Solvent | % by wt. of imine in solvent | Autoclave size [ml] | T [° C.] | p [bar] | Run time [h] | Conversion [based on imine] | RR/RS ratio |
|---|---|---|---|---|---|---|---|---|---|---|---|---|
| 7.1 | 2000 | Cu/Ni/Co (11/21/21) | ZrO$_2$ | 10 | ethylbenzene | 50 | 9000 | 120 | 100 | 42 | >99 | 99/1 |
| 7.2 | 40 | Cu/Ni/Co (3.3/3.3/3.3) | TiO$_2$ | 2.5 | methanol | 6 | 300 | 100 | 70 | 6 | 63 | 94/6 |
| 7.3 | 95 | Cu/Ni/Co (11/21/21) | ZrO$_2$ | 1.5 | methanol | 60 | 300 | 100 | 70 | 12 | >99 | 99/1 |
| 7.4 | 6800 | Cu/Ni/Co (11/21/21) | ZrO$_2$ | 7.5 | toluene/ethylbenzene | 63 | 20 000 | 120 | 100 | 48 | >99 | 98/2 |

V. General Method E

Diaselective hydrogenation of (R)-1,2-dimethylpropylidene-(1-phenylethyl)amine (Schiff base of (R)-(1-phenylethyl)amine with 3-methyl-2-butanone)

A 250 ml loop reactor (length=48.5 cm, diameter=2.5 cm, fill height=46.5 cm), which was operated continuously, was initially charged with a passivated Cu/Ni/Co catalyst on ZrO$_2$ with a metal loading of 11/21/21% by weight based on the total weight of the catalyst, and a 30% by weight solution of (R)-1,2-dimethylpropylidene(1-phenyl-ethyl)amine in the solvent specified in table 8 was hydrogenated with hydrogen under the reaction conditions specified in table 8 in continuous mode. A sample was taken from the output and analyzed by gas chromatography. The results from this are listed in table 8.

TABLE 8

| Example | Solvent | Loading [g/h * g cat] | T [° C.] | p [bar] | Conversion [based on imine] | RR/RS ratio |
|---|---|---|---|---|---|---|
| 8.1 | ethylbenzene | 0.05 | 100 | 100 | >99 | 98/2 |
| 8.2 | ethylbenzene | 0.07 | 100 | 100 | >99 | 98/2 |
| 8.3 | ethylbenzene | 0.05 | 80 | 100 | >99 | 98/2 |
| 8.4 | ethylbenzene | 0.05 | 60 | 100 | >99 | 98/2 |
| 8.5 | ethylbenzene | 0.05 | 40 | 100 | >99 | 98/2 |
| 8.6 | ethylbenzene | 0.05 | 40 | 70 | >99 | 98/2 |
| 8.7 | ethylbenzene | 0.05 | 50 | 70 | >99 | 98/2 |
| 8.8 | ethylbenzene | 0.05 | 50 | 50 | >99 | 98/2 |
| 8.9 | ethylbenzene | 0.09 | 50 | 50 | 97 | 98/2 |
| 8.10 | ethylbenzene | 0.09 | 70 | 50 | 98 | 98/2 |
| 8.11 | ethylbenzene | 0.09 | 70 | 70 | >99 | 98/2 |
| 8.12 | ethylbenzene | 0.09 | 100 | 100 | >99 | 98/2 |
| 8.13 | ethylbenzene | 0.14 | 100 | 100 | >99 | 98/2 |
| 8.14 | ethylbenzene | 0.18 | 100 | 100 | >99 | 98/2 |
| 8.15 | ethylbenzene | 0.18 | 80 | 100 | >99 | 98/2 |
| 8.16 | methanol | 0.04 | 100 | 100 | >99 | 98/2 |
| 8.17 | methanol | 0.06 | 100 | 100 | >99 | 98/2 |
| 8.18 | methanol | 0.09 | 100 | 100 | >99 | 98/2 |
| 8.19 | methanol | 0.04 | 100 | 70 | >99 | 98/2 |
| 8.20 | methanol | 0.04 | 100 | 50 | >99 | 98/2 |
| 8.21 | methanol | 0.04 | 80 | 50 | >99 | 98/2 |
| 8.22 | methanol | 0.04 | 60 | 50 | >99 | 98/2 |
| 8.23 | methanol | 0.04 | 40 | 50 | >99 | 98/2 |

VI. General Method F

Diaselective hydrogenation of (S)-1,2-dimethylpropylidene-(1-phenylethyl)amine (Schiff base of (S)-(1-phenylethyl)amine with 3-methyl-2-butanone)

A 250 ml loop reactor (length=48.5 cm, diameter=2.5 cm, fill height=46.5 cm), which was operated continuously, was initially charged with a passivated Cu/Ni/Mo catalyst on ZrO$_2$ with a metal loading of 13/40/1% by weight based on the total weight of the catalyst, and a 30% by weight solution of (S)-1,2-dimethylpropylidene(1-phenyl-ethyl)amine in methanol was hydrogenated with hydrogen under the reaction conditions specified in table 9 in continuous mode. A sample was taken from the output and analyzed by gas chromatography. The results from this are listed in table 9.

TABLE 9

| Example | Loading [g/h * g cat] | T [° C.] | p [bar] | Conversion [based on imine] | SS/SR ratio |
|---|---|---|---|---|---|
| 9.1 | 0.06 | 100 | 120 | 99 | 95/5 |
| 9.2 | 0.10 | 100 | 120 | 99 | 95/5 |
| 9.3 | 0.19 | 100 | 120 | 98 | 95/5 |
| 9.4 | 0.16 | 100 | 100 | >99 | 96/4 |
| 9.5 | 0.16 | 90 | 100 | >99 | 96/4 |
| 9.6 | 0.16 | 80 | 100 | >99 | 96/4 |
| 9.7 | 0.19 | 100 | 120 | 98 | 95/5 |
| 9.8 | 0.25 | 100 | 120 | 97 | 95/5 |

VII. General Method G

Diaselective hydrogenation of (R)-(1-cyclopropylidene)(1-phenylethyl)amine (Schiff base of (R)-(1-phenylethyl)amine with 1-cyclopropyl-1-ethanone)

315 mg of catalyst were introduced into a 15 ml autoclave and inertized with nitrogen. Subsequently, the catalyst was preactivated with hydrogen at a pressure of 50 bar at the temperature specified in table 10 for 2 hours. This was then followed by purging with nitrogen, cooling to room temperature at the same time, and then addition under nitrogen of a mixture of 3.5 ml of (R)-(1-cyclopropylidene)(1-phenylethyl)amine and 3.5 ml of ethylbenzene. Subsequently, hydrogen was injected until a pressure of about 20 bar was attained and the reaction mixture was heated to 100° C. On attainment of this temperature, the pressure was increased to 70 bar with hydrogen and the stirrer was started at 1000 rpm. After 3 hours under these reaction conditions, a sample was taken and was analyzed by gas chromatography. The results are reported in table 10 below.

TABLE 10

| Example | Catalyst [metal loading in % by wt.] | Support | Activation [° C.] | Conversion [based on imine] | RR/RS ratio |
|---|---|---|---|---|---|
| 10.1 | Cu/Ni/Mo (13/40/1) | ZrO$_2$ | 200 | 94 | 67/33 |
| 10.2 | Cu/Co/Mn/Mo/P (20/50/7/3/3) | unsupported | 300 | 32 | 67/33 |
| 10.3 | Cu/Ni/Co (3.3/3.3/3.3) | TiO$_2$ | 300 | 62 | 67/33 |
| 10.4 | Cu/Ni/Co (11/21/21) | ZrO$_2$ | 200 | 99 | 67/33 |
| 10.5 | Cu/Zn (32/32) | Al$_2$O$_3$ | 200 | 89 | 64/36 |

For comparison, under the same conditions, the reaction was carried out with a nickel/cobalt on titanium dioxide catalyst. The results are listed in table 11.

TABLE 11

| Comparative examples | | | | | |
|---|---|---|---|---|---|
| Example | Catalyst [metal loading in % by wt.] | Support | Activation [° C.] | Conversion [based on imine] | RR/RS ratio |
| 11.1 | Ni/Co (5/5) | TiO$_2$ | 300 | 30 | 67/33 |

Comparison of the results from tables 10 and 11 shows clearly that the addition of copper to the particular non-copper-containing catalysts a higher conversion can be achieved at comparable diastereoselectivity.

VIII. General Method H

Diaselective hydrogenation of (R)-(1-phenylethylidene)(1-phenylethyl)amine (Schiff base of (R)-(1-phenylethyl)amine with 1-phenyl-1-ethanone)

315 mg of catalyst were introduced into a 15 ml autoclave and inertized with nitrogen. Subsequently, the catalyst was preactivated with hydrogen at a pressure of 50 bar at the temperature specified in table 12 for 2 hours. This was then followed by purging with nitrogen, cooling to room temperature at the same time, and then addition under nitrogen of a mixture of 3.5 ml of (R)-(1-phenylethylidene)(1-phenylethyl)amine and 3.5 ml of ethylbenzene. Subsequently, hydrogen was injected until a pressure of about 20 bar was attained and the reaction mixture was heated to 100° C. On attainment of this temperature, the pressure was increased to 70 bar with hydrogen and the stirrer was started at 1000 rpm. After 3 hours under these reaction conditions, a sample was taken and was analyzed by gas chromatography. The results are reported in table 12 below.

TABLE 12

| Example | Catalyst [metal loading in % by wt.] | Support | Activation [° C.] | Conversion [based on imine] | RR/RS ratio |
|---|---|---|---|---|---|
| 12.1 | Cu/Ni/Mo (13/40/1) | ZrO$_2$ | 200 | >99 | 94/6 |
| 12.2 | Cu/Co/Mn/Mo/P (20/50/7/3/3) | unsupported | 300 | 53 | 98/2 |
| 12.3 | Cu/Ni/Co (3.3/3.3/3.3) | TiO$_2$ | 300 | 48 | 98/2 |
| 12.4 | Cu/Ni/Co (11/21/21) | ZrO$_2$ | 200 | >99 | 98/2 |
| 12.5 | Cu/Zn (32/32) | Al$_2$O$_3$ | 200 | >99 | 99/1 |

For comparison, under the same conditions, the reaction was carried out with a copper on titanium dioxide and a nickel/cobalt on titanium dioxide catalyst. The results are listed in table 13.

TABLE 13

| Comparative examples | | | | | |
|---|---|---|---|---|---|
| Example | Catalyst [metal loading in % by wt.] | Support | Activation [° C.] | Conversion [based on imine] | RR/RS ratio |
| 13.1 | Cu (10) | TiO$_2$ | 200 | 1 | 75/25 |
| 13.2 | Ni/Co (5/5) | TiO$_2$ | 300 | 47 | 96/4 |

Comparison of the results of tables 12 and 13 shows clearly that the addition of copper to the particular non-copper-containing catalysts leads to an increase in the diastereoselectivity.

IX. General Method I

Diaselective hydrogenation of (R)-1-phenylbutylidene(1-phenylethyl)amine (Schiff base of (R)-(1-phenylethyl)amine with 1-phenyl-1-butanone)

A mixture of 35% by weight of (R)-1-phenylbutylidene(1-phenylethyl)amine (imine) in methanol and passivated catalyst, as specified in table 14, was initially charged in each case in a 300 ml autoclave. This was followed by inertization with nitrogen and heating to 100° C. Subsequently, hydrogen was injected at this temperature up to a pressure of 100 bar and, when the internal pressure declined, brought back to the desired pressure. After 24 hours, measured from the injection of hydrogen, a sample was taken and was analyzed by gas chromatography. The results are reported in table 14 below.

TABLE 14

| Example | Imine [g] | Catalyst [metal loading in %] | Support | Catalyst: imine [% by wt.] | Conversion [based on imine] | RR/RS ratio |
|---|---|---|---|---|---|---|
| 14.1 | 48 | Cu/Ni/Co (11/21/21) | $ZrO_2$ | 5 | 98 | 98/2 |
| 14.2 | 48 | Cu/Ni/Mo (13/40/1) | $ZrO_2$ | 5 | 98 | 98/2 |

X. General Method J

Synthesis of the Imines

The imines (Schiff bases) can be synthesized by a modified method of Charles et al., Bull. Soc. Chim. Fr. 1970, 12, 4439-4446.

The ketone is initially charged with 1.25 eq. of your enantiomer of (1-phenylethyl)amine and 0.01 eq. of p-toluenesulfonic acid in toluene. The water of reaction which forms is removed continuously by means of azeotropic distillation. When no further conversion can be discerned by means of GC, the solvent is drawn off and the product is purified by means of a fractional distillation.

The invention claimed is:

1. A process, comprising diastereoselectively converting a chiral imine of formula I to an amine of formula II

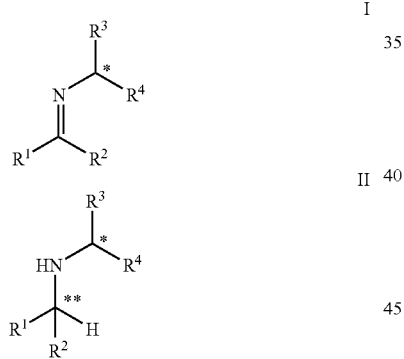

where $R^1$, $R^2$ are each $C_1$-$C_6$-alkyl, $C_3$-$C_6$-cycloalkyl, $C_2$-$C_6$-alkenyl, $C_2$-$C_6$-alkynyl, $C_2$-$C_6$-haloalkenyl, $C_2$-$C_6$-haloalkynyl, $C_1$-$C_6$-alkoxycarbonyl, $C_3$-$C_6$-alkenyloxycarbonyl, $C_3$-$C_6$-alkynyloxycarbonyl, aminocarbonyl, $C_1$-$C_6$-alkylaminocarbonyl, $C_3$-$C_6$-alkenylaminocarbonyl, $C_3$-$C_6$-alkynylamino-carbonyl, $C_1$-$C_6$-alkylsulfonylaminocarbonyl, di($C_1$-$C_6$-alkyl)aminocarbonyl, N—($C_3$-$C_6$-alkenyl)-N—($C_1$-$C_6$-alkyl)aminocarbonyl, N—($C_3$-$C_6$-alkynyl)-N—($C_1$-$C_6$-alkyeaminocarbonyl, N—($C_1$-$C_6$-alkoxy)-N—($C_1$-$C_6$-alkyl)aminocarbonyl, N—($C_3$-$C_6$-alkenyl)-N—($C_1$-$C_6$-alkoxy)aminocarbonyl, N—($C_3$-$C_6$-alkynyl)-N—($C_1$-$C_6$-alkoxy)aminocarbonyl, ($C_1$-$C_6$-alkyl)aminothiocarbonyl, di($C_1$-$C_6$-alkyl)aminothiocarbonyl or $C_1$-$C_6$-alkylcarbonyl-$C_1$-$C_6$-alkyl, where the alkyl, cycloalkyl and alkoxy radicals mentioned are optionally partially or fully halogenated and optionally have from one to three of: cyano, hydroxyl, $C_1$-$C_4$-alkyl, $C_3$-$C_6$-cycloalkyl, $C_1$-$C_6$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-alkylthio, amino, $C_1$-$C_4$-alkylamino, di($C_1$-$C_4$-alkyl)amino, $C_1$-$C_4$-alkylcarbonylamino, hydroxycarbonyl, $C_1$-$C_4$-alkoxycarbonyl, aminocarbonyl, $C_1$-$C_4$-alkylaminocarbonyl, di($C_1$-$C_4$-alkyl)aminocarbonyl or $C_1$-$C_4$-alkylcarbonyloxy;

aryl, aryl-$C_1$-$C_4$-alkyl, aryl-$C_2$-$C_4$-alkenyl, aryl-$C_2$-$C_4$-alkynyl, aryl-$C_1$-$C_4$-haloalkyl, aryl-$C_2$-$C_4$-haloalkenyl, aryl-$C_3$-$C_4$-haloalkynyl, aryl-$C_1$-$C_4$-hydroxyalkyl, arylcarbonyl-$C_1$-$C_4$-alkyl, aryl-$C_1$-$C_4$-alkylcarbonyl-$C_1$-$C_4$-alkyl, arylcarbonyloxy-$C_1$-$C_4$-alkyl, aryloxycarbonyl-$C_1$-$C_4$-alkyl, aryloxy-$C_1$-$C_4$-alkyl, arylamino-$C_1$-$C_4$-alkyl, arylthio-$C_1$-$C_4$-alkyl, arylsulfinyl-$C_1$-$C_4$-alkyl, arylsulfonyl-$C_1$-$C_4$-alkyl, heterocyclyl, heterocyclyl-$C_1$-$C_4$-alkyl, heterocyclyl-$C_2$-$C_4$-alkenyl, heterocyclyl-$C_2$-$C_4$-alkynyl, heterocyclyl-$C_1$-$C_4$-haloalkyl, heterocyclyl-$C_2$-$C_4$-haloalkenyl, heterocyclyl-$C_3$-$C_4$-haloalkynyl, heterocyclyl-$C_1$-$C_4$-hydroxyalkyl, heterocyclylcarbonyl-$C_1$-$C_4$-alkyl, heterocyclyl-$C_1$-$C_4$-alkyl-carbonyl-$C_1$-$C_4$-alkyl, heterocyclylcarbonyloxy-$C_1$-$C_4$-alkyl, heterocyclyloxycarbonyl-$C_1$-$C_4$-alkyl, heterocyclyloxy-$C_1$-$C_4$-alkyl, heterocyclylamino-$C_1$-$C_4$-alkyl, heterocyclylthio-$C_1$-$C_4$-alkyl, heterocyclylsulfinyl-$C_1$-$C_4$-alkyl, heterocyclylsulfonyl-$C_1$-$C_4$-alkyl, where the aforementioned radicals are optionally partially or fully halogenated and optionally have from one to three radicals from the group consisting of cyano, nitro, $C_1$-$C_6$-alkyl, $C_1$-$C_6$-haloalkyl, hydroxycarbonyl-$C_1$-$C_6$-alkyl, $C_1$-$C_4$-alkoxycarbonyl-$C_1$-$C_6$-alkyl, hydroxyl, $C_1$-$C_6$-hydroxyalkyl, $C_1$-$C_6$-alkoxy, $C_1$-$C_6$-haloalkoxy, hydroxycarbonyl, $C_1$-$C_6$-alkoxycarbonyl, aminocarbonyl, ($C_1$-$C_6$-alkyl)aminocarbonyl, di($C_1$-$C_6$-alkyl)aminocarbonyl, hydroxycarbonyl-$C_1$-$C_6$-alkoxy, $C_1$-$C_6$-alkoxycarbonyl-$C_1$-$C_6$-alkoxy, amino, $C_1$-$C_6$-alkylamino, di($C_1$-$C_6$-alkyl)amino, $C_1$-$C_6$-alkylsulfonylamino, $C_1$-$C_6$-haloalkyl-sulfonylamino, ($C_1$-$C_6$-alkyl)aminocarbonylamino, di($C_1$-$C_6$-alkyl)-aminocarbonylamino, aryl and aryl($C_1$-$C_6$-alkyl);

where the $R^1$ and $R^2$ radicals are different than one another;

$R^3$ is $C_1$-$C_6$-alkyl;

$R^4$ is aryl which is optionally partially or fully halogenated and optionally have from one to three radicals of cyano, nitro, $C_1$-$C_6$-alkyl, $C_1$-$C_6$-haloalkyl, hydroxyl, $C_1$-$C_6$-hydroxyalkyl, $C_1$-$C_6$-alkoxy, $C_1$-$C_6$-haloalkoxy, hydroxycarbonyl, $C_1$-$C_6$-alkoxycarbonyl, $C_1$-$C_6$-alkylamino, di($C_1$-$C_6$-alkyl)-amino, aryl and aryl($C_1$-$C_6$-alkyl);

and

\* represents a S or R configuration, and

\*\* represents at least one of S and R configurations;

wherein the conversion is carried out in the presence of hydrogen and a heterogeneous copper-containing catalyst, wherein the heterogeneous copper-containing catalyst comprises, based on the total weight of the catalyst, 0.1-95% by weight of copper, 0.1-85% by weight of at least one metal selected from the group consisting of nickel, cobalt and zinc;

0-15% by weight of at least one promoter selected from the group consisting of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium;

where a sum of the percentages by weight does not exceed 100%.

2. The process according to claim 1, wherein the copper-containing catalyst further comprises a support material.

3. The process according to claim 1, wherein the heterogeneous copper-containing catalyst further comprises, as a support material, carbon or a porous metal oxide selected from the group consisting of aluminum oxide, silicon dioxide, aluminosilicates, titanium dioxide, zirconium dioxide, magnesium oxide or mixtures thereof.

4. The process according to claim 1, wherein the copper-containing catalyst is an unsupported catalyst.

5. The process according to claim 1, wherein the conversion is carried out in the presence of a solvent.

6. The process according to claim 1, wherein the conversion is carried out at from standard pressure to 200 bar.

7. The process according to claim 1, wherein the conversion is carried out at from room temperature to reflux temperature of a reaction mixture.

8. The process according to claim 1, wherein
$R^3$ is $C_1$-$C_4$-alkyl, and
$R^4$ is aryl which is optionally partially or fully halogenated and optionally have from one to three radicals selected from the group consisting of cyano, nitro, $C_1$-$C_6$-alkyl, $C_1$-$C_6$-haloalkyl, $C_1$-$C_6$-alkoxy, $C_1$-$C_6$-haloalkoxy, aryl and aryl($C_1$-$C_6$-alkyl).

9. The process according to claim 1, wherein
$R^1$, $R^2$ are each $C_1$-$C_6$-alkyl, $C_3$-$C_6$-cycloalkyl, $C_2$-$C_6$-alkenyl, $C_2$-$C_6$-alkynyl, $C_2$-$C_6$-haloalkenyl, $C_2$-$C_6$-haloalkynyl or $C_1$-$C_6$-alkylcarbonyl-$C_1$-$C_6$-alkyl, where the alkyl, cycloalkyl and alkoxy radicals mentioned are optionally partially or fully halogenated and optionally have from one to three of: cyano, hydroxyl, $C_1$-$C_4$-alkyl, $C_3$-$C_6$-cycloalkyl, $C_1$-$C_6$-alkoxy-$C_1$-$C_4$-alkyl, $C_1$-$C_4$-alkoxy-$C_1$-$C_1$-$C_4$-alkoxy, $C_1$-$C_4$-alkylthio, amino, $C_1$-$C_4$-alkylamino, di($C_1$-$C_4$-alkyl)amino;

aryl, aryl-$C_1$-$C_4$-alkyl, aryl-$C_2$-$C_4$-alkenyl, aryl-$C_2$-$C_4$-alkynyl, aryl-$C_1$-$C_4$-haloalkyl, aryl-$C_2$-$C_4$-haloalkenyl, aryl-$C_3$-$C_4$-haloalkynyl, aryl-$C_1$-$C_4$-hydroxyalkyl, arylcarbonyl-$C_1$-$C_4$-alkyl, aryl-$C_1$-$C_4$-alkyl, carbonyl-$C_1$-$C_4$-alkyl, aryloxy-$C_1$-$C_4$-alkyl, arylthio-$C_1$-$C_4$-alkyl, arylsulfonyl-$C_1$-$C_4$-alkyl, heterocyclyl, heterocyclyl-$C_1$-$C_4$-alkyl, heterocyclyl-$C_2$-$C_4$-alkenyl, heterocyclyl-$C_2$-$C_4$-alkynyl, heterocyclyl-$C_1$-$C_4$-haloalkyl, heterocyclyl-$C_2$-$C_4$-haloalkenyl, heterocyclyl-$C_3$-$C_4$-haloalkynyl, heterocyclyl-$C_1$-$C_4$-hydroxyalkyl, heterocyclylcarbonyl-$C_1$-$C_4$-alkyl, heterocyclyl-$C_1$-$C_4$-alkylcarbonyl-$C_1$-$C_4$-alkyl, heterocyclyloxy-$C_1$-$C_4$-alkyl, heterocyclylamino-$C_1$-$C_4$-alkyl, heterocyclylthio-$C_1$-$C_4$-alkyl, heterocyclylsulfinyl-$C_1$-$C_4$-alkyl, heterocyclylsulfonyl-$C_1$-$C_4$-alkyl, where the aforementioned radicals are optionally partially or fully halogenated and optionally have from one to three radicals selected from the group consisting of cyano, nitro, $C_1$-$C_6$-alkyl, $C_1$-$C_6$-haloalkyl, hydroxyl, $C_1$-$C_6$-hydroxyalkyl, $C_1$-$C_6$-alkoxy, $C_1$-$C_6$-haloalkoxy, $C_1$-$C_6$-alkoxycarbonyl, di($C_1$-$C_6$-alkyl)aminocarbonyl, amino, $C_1$-$C_6$-alkylamino, di($C_1$-$C_6$-alkyl)amino, $C_1$-$C_6$-alkylsulfonylamino, $C_1$-$C_6$-haloalkylsulfonylamino, aryl and aryl($C_1$-$C_6$-alkyl).

10. A process for preparing an amine of formula II:

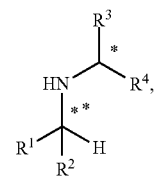

comprising
a) reacting a ketone of the formula III with an amine of the formula IV

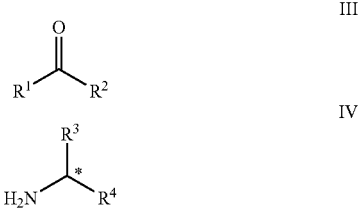

to obtain an imine of formula I

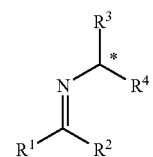

where
$R^1$, $R^2$ are each $C_1$-$C_6$-alkyl, $C_3$-$C_6$-cycloalkyl, $C_2$-$C_6$-alkenyl, $C_2$-$C_6$-alkynyl, $C_2$-$C_6$-haloalkenyl, $C_2$-$C_6$-haloalkynyl, $C_1$-$C_6$-alkoxycarbonyl, $C_3$-$C_6$-alkenyloxycarbonyl, $C_3$-$C_6$-alkynyloxycarbonyl, aminocarbonyl, $C_1$-$C_6$-alkylaminocarbonyl, $C_3$-$C_6$-alkenylaminocarbonyl, $C_3$-$C_6$-alkynylamino-carbonyl, $C_1$-$C_6$-alkylsulfonylaminocarbonyl, di($C_1$-$C_6$-alkyl)aminocarbonyl, N—($C_3$-$C_6$-alkenyl)-N—($C_1$-$C_6$-alkyl)aminocarbonyl, N—($C_3$-$C_6$-alkynyl)-N—($C_1$-$C_6$-alkyl)aminocarbonyl, N—($C_1$-$C_6$-alkoxy)-N—($C_1$-$C_6$-alkyl)aminocarbonyl, N—($C_3$-$C_6$-alkenyl)-N—($C_1$-$C_6$-alkoxy)aminocarbonyl, N—($C_3$-$C_6$-alkynyl)-N—($C_1$-$C_6$-alkoxy)aminocarbonyl, ($C_1$-$C_6$-alkyl)aminothiocarbonyl, di($C_1$-$C_6$-alkyl)aminothiocarbonyl or $C_1$-$C_6$-alkylcarbonyl-$C_1$-$C_6$-alkyl, where the alkyl, cycloalkyl and alkoxy radicals mentioned are optionally partially or fully halogenated and optionally have from one to three of: cyano, hydroxyl, $C_1$-$C_4$-alkyl, $C_3$-$C_6$-cycloalkyl, $C_1$-$C_6$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-alkylthio, amino, $C_1$-$C_4$-alkylamino, di($C_1$-$C_4$-alkyl)amino, $C_1$-$C_4$-alkylcarbonylamino, hydroxycarbonyl, $C_1$-$C_4$-alkoxycarbonyl, aminocarbonyl, $C_1$-$C_4$-alkylaminocarbonyl, di($C_1$-$C_4$-alkyl)aminocarbonyl or $C_1$-$C_4$-alkylcarbonyloxy;

aryl, aryl-$C_1$-$C_4$-alkyl, aryl-$C_2$-$C_4$-alkenyl, aryl-$C_2$-$C_4$-alkynyl, aryl-$C_1$-$C_4$-haloalkyl, aryl-$C_2$-$C_4$-haloalkenyl, aryl-$C_3$-$C_4$-haloalkynyl, aryl-$C_1$-$C_4$-hydroxyalkyl, arylcarbonyl-$C_1$-$C_4$-alkyl, aryl-$C_1$-$C_4$-alkylcarbonyl-$C_1$-$C_4$-alkyl, arylcarbonyloxy-$C_1$-$C_4$-alkyl, aryloxycarbonyl-$C_1$-$C_4$-alkyl, aryloxy-$C_1$-$C_4$-alkyl, arylamino-$C_1$-$C_4$-alkyl, arylthio-$C_1$-$C_4$-alkyl, arylsulfinyl-$C_1$-$C_4$-alkyl, arylsulfonyl-$C_1$-$C_4$-alkyl, heterocyclyl, heterocyclyl-$C_1$-$C_4$-alkyl, heterocyclyl-$C_2$-$C_4$-alkenyl, heterocyclyl-$C_2$-$C_4$-alkynyl, heterocyclyl-$C_1$-$C_4$-haloalkyl, heterocyclyl-$C_2$-$C_4$-haloalkenyl, heterocyclyl-$C_3$-$C_4$-haloalkynyl, heterocyclyl-$C_1$-$C_4$-hydroxyalkyl, heterocyclylcarbonyl-$C_1$-$C_4$-alkyl, heterocyclyl-$C_1$-$C_4$-alkyl-carbonyl-$C_1$-$C_4$-alkyl, heterocyclylcarbonyloxy-$C_1$-$C_4$-alkyl, heterocyclyloxycarbonyl-$C_1$-$C_4$-alkyl, heterocyclyloxy-$C_1$-$C_4$-alkyl, heterocyclylamino-$C_1$-$C_4$-alkyl, heterocyclylthio-$C_1$-$C_4$-alkyl, heterocyclylsulfinyl-$C_1$-$C_4$-alkyl, heterocyclylsulfonyl-$C_1$-$C_4$-alkyl, where the aforementioned radicals of are partially or fully halogenated and optionally have from one to three radicals from the group consisting of cyano, nitro, $C_1$-$C_6$-alkyl, $C_1$-$C_6$-haloalkyl, hydroxycarbonyl-$C_1$-$C_6$-alkyl, $C_1$-$C_4$-alkoxycarbonyl-$C_1$-$C_6$-alkyl, hydroxyl, $C_1$-$C_6$-hydroxyalkyl, $C_1$-$C_6$-alkoxy, $C_1$-$C_6$-haloalkoxy, hydroxycarbonyl, $C_1$-$C_6$-alkoxycarbonyl, aminocarbonyl, ($C_1$-$C_6$-alkyl)aminocarbonyl, di($C_1$-$C_6$-alkyl)aminocarbonyl, hydroxycarbonyl-$C_1$-$C_6$-alkoxy, $C_1$-$C_6$-alkoxycarbonyl-$C_1$-$C_6$-alkoxy, amino, $C_1$-$C_6$-alkylamino, di($C_1$-$C_6$-alkyl)amino, $C_1$-$C_6$-alkylsulfonylamino, $C_1$-$C_6$-haloalkylsulfonylamino, ($C_1$-$C_6$-alkyl)aminocarbonylamino, di($C_1$-$C_6$-alkyl)-aminocarbonylamino, aryl and aryl($C_1$-$C_6$-alkyl);

where the $R^1$ and $R^2$ radicals are different than one another;

$R^3$ is $C_1$-$C_6$-alkyl;

$R^4$ is aryl which is optionally partially or fully halogenated and optionally have from one to three radicals from the group consisting of cyano, nitro, $C_1$-$C_6$-alkyl, $C_1$-$C_6$-haloalkyl, hydroxyl, $C_1$-$C_6$-hydroxyalkyl, $C_1$-$C_6$-alkoxy, $C_1$-$C_6$-haloalkoxy, hydroxycarbonyl, $C_1$-$C_6$-alkoxycarbonyl, $C_1$-$C_6$-alkylamino, di($C_1$-$C_6$-alkyl)amino, aryl and aryl($C_1$-$C_6$-alkyl);

and

** represents a S or R configuration, and represents at least one of S and R configurations;

and then b) reacting the imine of the formula I obtained from a) with hydrogen and a heterogeneous copper-containing catalyst, to form an amine of formula II, where the heterogeneous copper-containing catalyst comprises, based on the total weight of the catalyst, 0.1-95% by weight of copper, 0.1-85% by weight of at least one metal selected from the group of nickel, cobalt and zinc;

0-15% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium;

where a sum of the percentages by weight does not exceed 100%.

11. The process according to claim 10, wherein the imine of the formula I is prepared in the presence of an acid or of a heterogeneous catalyst selected from the group consisting of aluminum oxide, titanium dioxide, zirconium dioxide, silicon oxide and clay mineral, and mixtures thereof.

12. The process according to claim 10, comprising:

a) reacting a ketone of the formula III with an amine of the formula IV

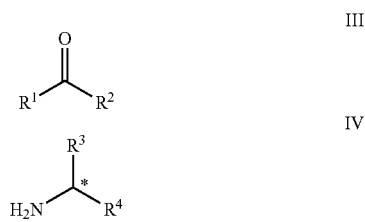

to prepare the imine according to formula I

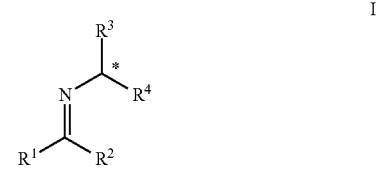

where $R^1$, $R^2$ are each $C_1$-$C_6$-alkyl, $C_3$-$C_6$-cycloalkyl, $C_2$-$C_6$-alkenyl, $C_2$-$C_6$-alkynyl, $C_2$-$C_6$-haloalkenyl, $C_2$-$C_6$-haloalkynyl, $C_1$-$C_6$-alkoxycarbonyl, $C_3$-$C_6$-alkenyloxycarbonyl, $C_3$-$C_6$-alkynyloxycarbonyl, aminocarbonyl, $C_1$-$C_6$-alkylaminocarbonyl, $C_3$-$C_6$-alkenylaminocarbonyl, $C_3$-$C_6$-alkynylaminocarbonyl, $C_1$-$C_6$-alkylsulfonylaminocarbonyl, di($C_1$-$C_6$-alkyl)aminocarbonyl, N—($C_3$-$C_6$-alkenyl)-N—($C_1$-$C_6$-alkyl)aminocarbonyl, N—($C_3$-$C_6$-alkynyl)-N—($C_1$-$C_6$-alkyl)aminocarbonyl, N—($C_1$-$C_6$-alkoxy)-N—($C_1$-$C_6$-alkyl)aminocarbonyl, N—($C_3$-$C_6$-alkenyl)-N—($C_1$-$C_6$-alkoxy)aminocarbonyl, N—($C_3$-$C_6$-alkynyl)-N—($C_1$-$C_6$-alkoxy)aminocarbonyl, ($C_1$-$C_6$-alkyl)aminothiocarbonyl, di($C_1$-$C_6$-alkyl)aminothio-carbonyl or $C_1$-$C_6$-alkylcarbonyl-$C_1$-$C_6$-alkyl, where the alkyl, cycloalkyl and alkoxy radicals mentioned are optionally partially or fully halogenated and optionally have from one to three of: cyano, hydroxyl, $C_1$-$C_4$-alkyl, $C_3$-$C_6$-cycloalkyl, $C_1$-$C_6$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-alkylthio, amino, $C_1$-$C_4$-alkylamino, di($C_1$-$C_4$-alkyl)amino, $C_1$-$C_4$-alkylcarbonylamino, hydroxycarbonyl, $C_1$-$C_4$-alkoxycarbonyl, aminocarbonyl, $C_1$-$C_4$-alkylaminocarbonyl, di($C_1$-$C_4$-alkyl)aminocarbonyl or $C_1$-$C_4$-alkylcarbonyloxy;

aryl, aryl-$C_1$-$C_4$-alkyl, aryl-$C_2$-$C_4$-alkenyl, aryl-$C_2$-$C_4$-alkynyl, aryl-$C_1$-$C_4$-haloalkyl, aryl-$C_2$-$C_4$-haloalkenyl, aryl-$C_3$-$C_4$-haloalkynyl, aryl-$C_1$-$C_4$-hydroxy-alkyl, arylcarbonyl-$C_1$-$C_4$-alkyl, aryl-$C_1$-$C_4$-alkylcarbonyl-$C_1$-$C_4$-alkyl, arylcarbonyloxy-$C_1$-$C_4$-alkyl, aryloxycarbonyl-$C_1$-$C_4$-alkyl, aryloxy-$C_1$-$C_4$-alkyl, arylamino-$C_1$-$C_4$-alkyl, arylthio-$C_1$-$C_4$-alkyl, arylsulfinyl-$C_1$-$C_4$-alkyl, arylsulfonyl-$C_1$-$C_4$-alkyl, heterocyclyl, heterocyclyl-$C_1$-$C_4$-alkyl, heterocyclyl-$C_2$-$C_4$-alkenyl, heterocyclyl-$C_1$-$C_4$-alkynyl, heterocyclyl-$C_1$-$C_4$-haloalkyl, heterocyclyl-$C_1$-$C_4$-haloalkenyl, heterocyclyl-$C_3$-$C_4$-haloalkynyl, heterocyclyl-$C_1$-$C_4$-hydroxyalkyl, heterocyclylcarbonyl-$C_1$-$C_4$-alkyl, heterocyclyl-$C_1$-$C_4$-alkyl-carbonyl-$C_1$-$C_4$-alkyl, heterocyclylcarbonyloxy-$C_1$-$C_4$-alkyl, heterocyclyloxycarbonyl-$C_1$-$C_4$-alkyl, heterocyclyloxy-$C_1$-$C_4$-alkyl, heterocyclylamino-$C_1$-$C_4$-alkyl, heterocyclylthio-$C_1$-$C_4$-alkyl, heterocyclylsulfinyl-$C_1$-$C_4$-alkyl, heterocyclylsulfonyl-$C_1$-$C_4$-alkyl, where the aforementioned radicals are optionally partially or fully halogenated and optionally have from one to three radicals from the group consisting of cyano, nitro, $C_1$-$C_6$-alkyl, $C_1$-$C_6$-haloalkyl, hydroxy-carbonyl-$C_1$-$C_6$-alkyl, $C_1$-$C_4$-alkoxycarbonyl-$C_1$-$C_6$-alkyl, hydroxyl, $C_1$-$C_6$-hydroxyalkyl, $C_1$-$C_6$-alkoxy, $C_1$-$C_6$-haloalkoxy, hydroxycarbonyl, $C_1$-$C_6$-alkoxycarbonyl, aminocarbonyl, ($C_1$-$C_6$-alkyl) aminocarbonyl, di($C_1$-$C_6$-alkyl)aminocarbonyl, hydroxycarbonyl-$C_1$-$C_6$-alkoxy, $C_1$-$C_6$-alkoxycarbonyl-$C_1$-$C_6$-alkoxy, amino, $C_1$-$C_6$-alkylamino, di($C_1$-$C_6$-alkyl)amino, $C_1$-$C_6$-alkylsulfonylamino, $C_1$-$C_6$-haloalkylsulfonylamino, ($C_1$-$C_6$-alkyl)aminocarbonylamino, di($C_1$-$C_6$-alkyl)aminocarbonylamino, aryl and aryl($C_1$-$C_6$-alkyl);

where the $R^1$ and $R^2$ radicals are different than one another;
$R^3$ is $C_1$-$C_6$-alkyl;
$R^4$ is aryl which is optionally partially or fully halogenated and optionally have from one to three radicals from the group consisting of cyano, nitro, $C_1$-$C_6$-alkyl, $C_1$-$C_6$-haloalkyl, hydroxyl, $C_1$-$C_6$-hydroxyalkyl, $C_1$-$C_6$-alkoxy, $C_1$-$C_6$-haloalkoxy, hydroxycarbonyl, $C_1$-$C_6$-alkoxy-carbonyl, $C_1$-$C_6$-alkylamino, di($C_1$-$C_6$-alkyl) amino, aryl and aryl($C_1$-$C_6$-alkyl);
b) reacting the imine of the formula I obtained from a) with hydrogen and a heterogeneous copper-containing catalyst, to form an amine of formula II

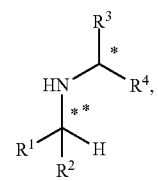

where the heterogeneous copper-containing catalyst comprises, based on the total weight of the catalyst,
0.1-95% by weight of copper,
0.1-85% by weight of at least one metal selected from the group of nickel, cobalt and zinc;
0-15% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium;
where the sum of the percentages by weight does not exceed 100%;
c) subsequently hydrogenolytically cleaving the amine of the formula II obtained from step b), to form a chiral amine of formula VIII

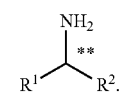

13. The process according to claim 12, wherein the hydrogenolysis is carried out by hydrogen in the presence of a heterogeneous catalyst selected from the group consisting of the platinum metal elements.

14. The process according to claim 13, wherein the hydrogenolysis is carried out with metal hydrides or mixtures of metal hydrides.

15. The process according to claim 1, wherein the process is carried out continuously, semicontinuously or batchwise.

16. The process according to claim 1, where a parent amine of the chiral imine is chiral and a parent ketone of the chiral imine is prochiral.

* * * * *